United States Patent [19]

Hamanaka et al.

[11] 4,389,413
[45] Jun. 21, 1983

[54] 9,11-METHANO-13-AZA-11A-CARBATH-ROMBANOIC ACID ANALOGUES

[76] Inventors: Nobuyuki Hamanaka, 11-38, Koaza Hiroshiki, Ooaza Ooyamazaki, Ooyamazaki-cho, Otokuni-gun, Kyoto; Shinsuke Hashimoto, 3-2, Matsunami-cho, Nishinomiya-city, Hyogo; Masaki Hayashi, 5-10, Nanpeidai 4-chome, Takatsuki-city, Osaka, all of Japan

[21] Appl. No.: 285,723

[22] Filed: Jul. 22, 1981

[30] Foreign Application Priority Data

Jul. 22, 1980 [JP] Japan .................................. 55-99371
Dec. 26, 1980 [JP] Japan .................................. 55-183762

[51] Int. Cl.³ .................. A61K 31/557; C07C 101/14
[52] U.S. Cl. .................................... 424/305; 260/404; 424/309; 424/319; 560/9; 560/18; 560/45; 560/48; 560/116; 560/118; 562/427; 562/452; 562/457; 562/498; 562/500
[58] Field of Search ................... 560/118, 45, 48, 116, 560/18, 9; 562/500, 452, 457, 498, 427; 424/305, 309, 319; 260/404

[56] References Cited

U.S. PATENT DOCUMENTS

| | | | |
|---|---|---|---|
| 4,182,903 | 1/1980 | Favara et al. | 562/503 |
| 4,188,403 | 2/1980 | Orth et al. | 424/330 |
| 4,239,778 | 12/1980 | Venton et al. | 424/305 |
| 4,260,806 | 4/1981 | Nicolaou et al. | 560/118 |

FOREIGN PATENT DOCUMENTS 55-5143930  11/1980  Japan .................................. 560/118

OTHER PUBLICATIONS

Fried et al., Advances in Prostaglandin & Thromboxane Research, vol. 6, p. 427 (1980).

Primary Examiner—Robert Gerstl

[57] ABSTRACT

The 9,11-methano-13-aza-11a-carbathrombanoic acid analogues of the general formula:

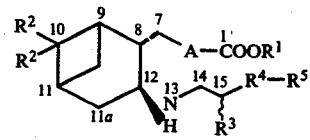

V

[wherein A represents

—CH₂CH₂—(CH₂)ₘ—,    (i)

-continued

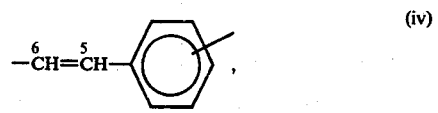

(in which m is an integer of 1 to 6, the double bond between the carbon atoms in positions 5 and 6 in (iv) is in cis or trans-configuration or a mixture thereof and the phenylene group in (iv) represents o-, m- or p-phenylene), $R^1$ represents a hydrogen atom or a straight- or branched-chain alkyl group of 1 to 12 carbon atoms, two $R^2$ both represent hydrogen atoms or methyl groups, $R^3$ represents a hydrogen atom or a hydroxy group, $R^4$ represents a single bond or a straight- or branched-chain alkylene group of 1 to 5 carbon atoms, $R^5$ represents (i) a straight- or branched-chain alkyl, alkoxy or alkylthio group of 1 to 8 carbon atoms,
(ii) a cycloalkyl or cycloalkyloxy group of 4 to 7 carbon atoms being unsubstituted or substituted by at least one straight- or branched-chain alkyl group of 1 to 8 carbon atoms or

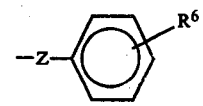

in which Z represents a single bond, an oxygen atom or a sulfur atom and $R^6$ may occupy any of the free positions on the phenyl ring and represents a hydrogen atom, a halogen atom, a hydroxy group, a straight- or branched-chain alkyl or alkoxy group of 1 to 5 carbon atoms, a trihalomethyl group, an amino group or a mono- or dialkyl-amino group of 1 to 5 carbon atoms)

and the wavy line attached to the carbon atom in position 15 represents α- or β-configuration or a mixture thereof, provided that, when $R^3$ represents a hydroxy group and $R^4$ represents a single bond, $R^5$ does not represent an alkoxy group, an alkylthio group, a cycloalkyloxy group, a phenoxy group and a phenylthio group], and cyclodextrin clathrates thereof, and when $R^1$ represents a hydrogen atom, non-toxic salts thereof, possess strong inhibitory activities on platelet aggregation and on aorta contraction, and are useful for prevention and treatment of diseases which are induced by thromboxane $A_2$.

43 Claims, No Drawings

9,11-METHANO-13-AZA-11A-CARBATHROMBANOIC ACID ANALOGUES

This invention relates to new 9,11-methano-13-aza-11a-carbathrombanoic acid analogues having inhibitory activity on platelet aggregation and inhibitory activity on aorta contraction.

In 1975, Hamberg et al discovered an unstable intermediate in the conversion of prostaglandin $G_2$ into the hemiacetal derivative in platelets [Proc. Nat. Acad. Sci. USA, vol 72, No. 8, page 2994–2998 (1975)]. The intermediate has been named as thromboxane $A_2$ and its structure has been proposed as follows:

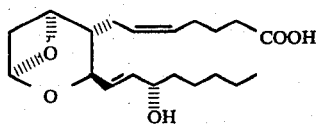
I

Thromboxane $A_2$ has been found to show various biological acitivities such as platelet aggregation, aorta contraction and thrombi formation and, therefore is considered to be one of the causes by which diseases such as inflammation, thrombus and cardiac infarction are induced.

Recently we have proposed new compounds of the following formula:

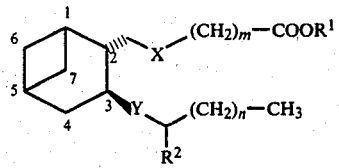
II (wherein X is ethylene or cis-vinylene, Y is ethylene, vinylene or ethynylene, $R^1$ is a hydrogen atom or an alkyl group of 1 to 12 carbon atoms, $R^2$ is a hydrogen atom or a hydroxy group, m is an integer of 1 to 6 and n is an integer of 1 to 8), antagonizing the action of thromboxane $A_2$ [cf. Japanese Patent Kokai No. 143930/80 (Derwent No. 01020D)].

Furthermore, two compounds of the following formulae:

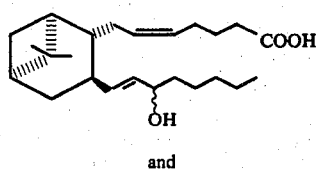
III and

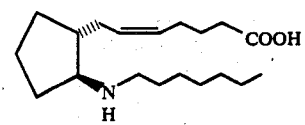
IV have reported as antagonists of thromboxane $A_2$ [cf. Proc. Nat. Acad. Sci. USA, vol. 76, No. 6, page 2566–2570 (1979) and ibid, vol. 76, No. 8, page 4097–4101 (1979), respectively], after our proposal.

However the compounds of formulae II, III and IV are unsatisfactory as practically effective medicines since they have no or very weak inhibitory activities on platelet aggregation and on aorta contraction.

As a result of extensive research and experimentation to discover novel compounds having potent antagonistic activity on thromboxane $A_2$, it has now been found that by replacing groups represented by the symbol Y, by an iminomethylene group (i.e. —NHCH$_2$—) and by introducing or not two methyl groups at the 7-position of the norpinane skeleton in compounds of the general formula II, the activity of new compounds is enhanced.

Accordingly, the present invention provides new 9,11-methano-13-aza-11a-carbathrombanoic acid analogues of the general formula:

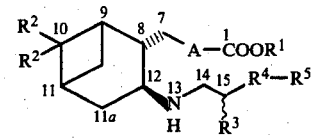
V

[wherein A represents $-CH_2CH_2-(CH_2)_m-$,  (i)

$-CH\overset{cis}{=\!=\!=}CH-(CH_2)_m-$,  (ii)

$-CH_2-O-(CH_2)_m-$ or  (iii)

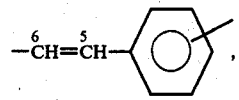
(iv)

(in which m is an integer of 1 to 6, the double bond between the carbon atoms in positions 5 and 6 in (iv) is in cis or trans-configuration (i.e. E or Z configuration) or a mixture thereof (i.e. EZ) and the phenylene group in (iv) represents o-, m- or p-phenylene), $R^1$ represents a hydrogen atom or a straight-or branched-chain alkyl group of 1 to 12 carbon atoms, two $R^2$ both represent hydrogen atoms or methyl groups, $R^3$ represents a hydrogen atom or a hydroxy group, $R^4$ represents a single bond or a straight- or branched-chain alkylene group of 1 to 5 carbon atoms, $R^5$ represents (i) a straight- or branched-chain alkyl, alkoxy or alkylthio group of 1 to 8 carbon atoms, (ii) a cycloalkyl or cycloalkyloxy group of 4 to 7 carbon atoms being unsubstituted or substituted by at least one straight- or branched-chain alkyl group of 1 to 8 carbon atoms or (iii)

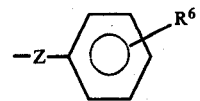

(in which Z represents a single bond, an oxygen atom or a sulfur atom and $R^6$ may occupy any of the free positions on the phenyl ring and represents a hydrogen atom, a halogen atom, a hydroxy group, a straight- or branched-chain alkyl or alkoxy group of 1 to 5 carbon atoms, a trihalomethyl group, an amino group or a mono- or dialkyl-amino group of 1 to 5 carbon atoms) and the wavy line ∽ attached to the carbon atom in position 15 represents α- or β-configuration (i.e. S- or R-configuration) or a mixture thereof (i.e. RS), provided that, when $R^3$ represents a hydroxy group and $R^4$ represents a single bond, $R^5$ does not represent an alkoxy group, an alkylthio group, a cycloalkyloxy group, a phenoxy group and a phenylthio group], and cyclodextrin clathrates thereof, and when $R^1$ represents a hydrogen atom, non-toxic salts thereof.

Throughout the specification including claims, the 11a-carbathrombanoic acid has a skeleton structure as shown in the following formula, and a compound having one double bond is designated as a 11a-carbathromb-enoic acid [cf. Prostaglandins, 16(6), 857 (1978)].

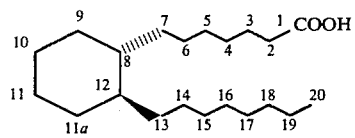

VI

In the structural formulae of the specification, the dotted line, the thick line—, and the wavy line indicate that the respective group attached thereto is in the backside of the plane, i.e. in α-configuration, in the front side of the plane, i.e. in β-configuration, and in α- or β-configuration or a mixture thereof, respectively, according to the rules of the generally accepted nomenclature.

This invention relates to the compounds represented by the formula V, i.e. an optically active 'natural form' or an enantiomer thereof or a mixture thereof, particularly, a racemic form comprising an eqivalent mixture of the 'natural form' and the enantiomer thereof.

As is obvious to those skilled in the art, the compounds represented by the general formula V have at least two asymmetric centers, and these two asymmetric centres are carbon atoms at the 8- and 12-positions. When the alkyl group and the alkylene group represent a branched-chain, there is a possibility that other asymmetric centers are formed. The existence of an asymmetric center forms isomers as is well known. However, the compounds represented by the general formula V have substituents attached to the 8- and 12-positioned carbon atoms of the bicyclo ring in trans-configuration. Therefore, the isomers of the compounds of the general formula V wherein the substituents attached to the 8- and 12-positioned carbon atoms have trans-configuration, and mixtures thereof are included in the range of the compounds represented by the general formula V.

Examples of the group —$(CH_2)_m$— in the symbol A in the compounds of the general formula V are methylene, ethylene, trimethylene, tetramethylene, pentamethylene and hexamethylene; preferably the group —$(CH_2)_m$— represents a trimethylene group.

Examples of the alkyl groups represented by $R^1$ are methyl, ethyl, propyl, butyl, pentyl, hexyl, heptyl, octyl, nonyl, decyl, undecyl and dodecyl and isomers thereof; $R^1$ preferably represents a hydrogen atom or an alkyl group of 1 to 4 carbon atoms, i.e. methyl, ethyl, propyl, isopropyl, butyl, isobutyl, sec-butyl or tert-butyl; most preferably $R^1$ represents a hydrogen atom or a methyl group.

Examples of the alkylene groups represented by $R^4$ are methylene, ethylene, trimethylene, tetramethylene and pentamethylene and isomers thereof; $R^4$ preferably represents a single bond or a methylene, methylmethylene, ethylene or 1-methylethylene group.

Examples of the alkyl, alkoxy and alkylthio groups represented by $R^5$ are methyl, ethyl, propyl, 1-methylpropyl, 2-methylpropyl, butyl, 1-methylbutyl, 2-methylbutyl, pentyl, 1-methylpentyl, 2-methylpentyl, hexyl, 1-methylhexyl, 2-methylhexyl, and ethoxy, propoxy, butoxy, pentyloxy, hexyloxy, ethylthio, propylthio, butylthio, pentylthio, hexylthio and isomers thereof.

Examples of the cycloalkyl and cycloalkyloxy groups represented by $R^5$ are cyclobutyl, 1-propylcyclobutyl, 1-butylcyclobutyl, 1-pentylcyclobutyl, 1-hexylcyclobutyl, cyclopentyl, 3-methylcyclopentyl, 3-ethylcyclopentyl, 3-propylcyclopentyl, 3-butylcyclopentyl, 3-tert-butylcyclopentyl, cyclohexyl, 3-methylcyclohexyl, 3-ethylcyclohexyl, 3-propylcyclohexyl, 3-isopropylcyclohexyl, 3-butylcyclohexyl, 4-methylcyclohexyl, 4-ethylcyclohexyl, 4-propylcyclohexyl, 4-tert-butylcyclohexyl, cycloheptyl, cyclobutyloxy, cyclopentyloxy, cyclohexyloxy and cycloheptyloxy.

Examples of the groups of the formula

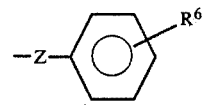

represented by $R^5$ are phenyl, phenoxy and phenylthio groups and these groups having a chlorine atom, a fluorine atom, a hydroxy group, a straight- or branched-chain alkyl group of 1 to 5 carbon atoms, a trifluoromethyl group, a methoxy group, an ethoxy group, an amino group, a methyamino group, an ethylamino group, a dimethylamino group or a diethylamino group at one carbon atom of the benzene ring thereof.

Preferably the group —$R^4$—$R^5$ represents pentyl, 1-methylpentyl, 2-methylpentyl, hexyl, 1-methylhexyl, 2-methylhexyl, heptyl, 1-methylheptyl, 2-methylheptyl, octyl, pentyloxymethyl, pentylthiomethyl, 1-propylcyclobutyl, 1-butylcyclobutyl, 1-pentylcyclobutyl, 1-hexylcyclobutyl, cyclopentyl, cyclopentylmethyl, 3-methylcyclopentyl, 3-ethylcyclopentyl, 3-propylcyclopentyl, 3-butylcyclopentyl, cyclohexyl, cyclohexylmethyl, 3-methylcyclohexyl, 3-ethylcyclohexyl, 3-propylcyclohexyl, 3-butylcyclohexyl, 4-methylcyclohexyl, 4-ethylcyclohexyl, 4-propylcyclohexyl, cycloheptyl, cyclopentyloxymethyl, phenyl, benzyl, 2-phenylethyl, phenoxymethyl, 3- or 4-methylphenoxymethyl, 3- or 4-ethylphenoxymethyl, 3- or 4-propylphenoxymethyl, 3- or 4-tert-butylphenoxymethyl, 3- or 4-chlorophenoxymethyl, 3-or 4-trifluoromethylphenoxymethyl, 3- or 4-fluorophenoxymethyl, 3- or 4-hydroxyphenoxymethyl, 3- or 4-aminophenoxymethyl, phenylthiomethyl, 3- or 4-methylphenylthiomethyl, 3- or 4-ethylphenylthiomethyl, 3- or 4-propylphenylthiomethyl, 3- or 4-tert-butylphenylthiomethyl, 3- or 4-chlorophenylthiomethyl, 3- or 4-trifluoromethylphenylthiomethyl, 3- or 4-fluorophenylthiomethyl, 3- or 4-hydroxyphenylthiomethyl and 3- or 4-aminophenylthiomethyl.

11a-Carbathrombanoic acid analogues of general formula V wherein A represents the group

$R^1$ represents a hydrogen atom or a methyl group, two $R^2$ represent methyl groups, $R^3$ represents a hydroxy group and the group —$R^4$—$R^5$ represents a straight- or branched-chain alkyl or alkylthio group of 4 to 9 carbon atoms, or a phenoxymethyl or phenylthiomethyl group unsubstituted or substituted by methyl, ethyl, propyl, chlorine or trifluoromethyl at the 3 or 4 position of the benzene ring thereof, are most preferred.

According to a feature of the present invention, 11a-carbathrombanoic acid analogues of general formula V, wherein $R^3$ represents a hydroxy group and the other symbols are as hereinbefore defined, i.e. compounds of the general formula:

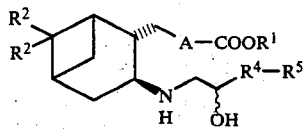  VA (wherein the various symbols are as hereinbefore defined) may be prepared by reacting a compound of the general formula:

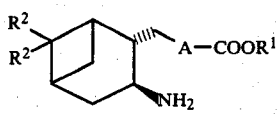  VII (wherein the various symbols are as hereinbefore defined) with a compound of the general formula:

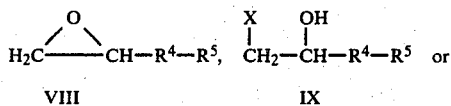

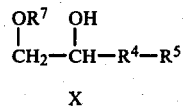
X (wherein X represents a halogen atom, $R^7$ represents a tosyl group or a mesyl group and the other symbols are as hereinbefore defined).

This reaction may be carried out by methods known per se, and, for example, in an inert organic solvent such as a lower alkanol, e.g. methanol or ethanol, methylene chloride or chloroform at a temperature from 0° C. to a refluxing temperature of the solvent. By the expression 'methods known per se' as used in this specification is meant methods heretofore used or described in the chemical literature.

The compounds of the general formulae VIII, IX and X are well known per se, and can be obtained from known compounds by methods known per se.

11a-Carbathrombanoic acid analogues of general formula V, wherein $R^3$ represents a hydrogen atom and the other symbols are as hereinbefore defined, i.e. compounds of the general formula:

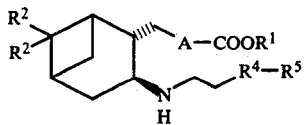  VB (wherein various symbols are as hereinbefore defined) may be prepared by reacting a compound of the general formula VII with a compound of the general formula:

$R^5-R^4-CH_2CHO$   XI (wherein the various symbols are as hereinbefore defined) to dehydration, and subjecting the resulting compounds of the general formula:

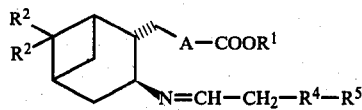  XII (wherein the various symbols are as hereinbefore defined), to the reaction for reducing the imino group to an amino group.

The dehydration reaction can be carried out in the presence of Molecular Sieves 3A or 4A in an inert organic solvent, such as an alkanol of 1 to 4 carbon atoms, e.g. methanol or ethanol, methylene chloride or chloroform, at a temperature ranging from a refluxing temperature of the solvent to 0° C. Molecular Sieves may be pellets or powders, preferable powders. The reaction to convert the imino group to amino group can be performed by methods known per se, for example, using sodium borohydride in methanol at 0° C.

Compounds of the general formula XI are well known, and can be prepared from known compounds by methods known per se.

Starting materials of the general formula VII, wherein A represents

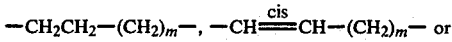

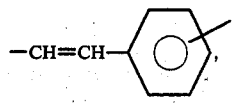

in which m is as hereinbefore defined, i.e. compounds of the general formula:

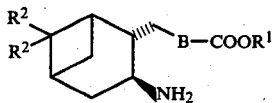  VIIA

[wherein B represents $-CH_2CH_2-(CH_2)_m-$,  (i)

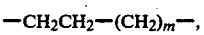  (ii)

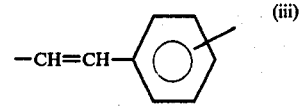  (iii)

(in which m and the double bond and the phenylene group in (iii) are as hereinbefore defined) and the other symbols are as hereinbefore defined] may be prepared by the series of reactions depicted schematically below in Scheme A, wherein THP represents a tetrahydropyran-2-yl group, Ms represents a mesyl group and the other symbols are as hereinbefore defined.

Scheme A

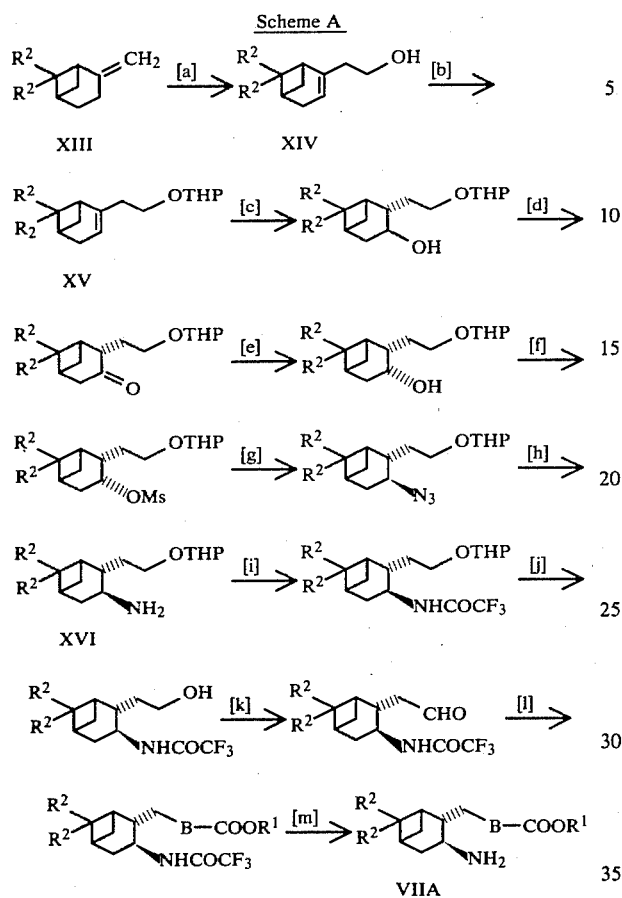

In the Scheme A, each step can be effected using methods known per se. For example, step [a] can be carried out by heating in a sealed tube using paraformaldehyde; step [b] can be conducted by using 2,3-dihydropyran in methylene chloride in the presence of p-toluenesulfonic acid; step [c] can be conducted by using diborane in tetrahydrofuran; step [d] can be performed by using a chromic acid solution in diethyl ether; step [e] can be conducted by reacting using sodium borohydride in methanol at 0° C.; step [f] can be conducted by reacting using methanesulfonyl chloride in methylene chloride in the presence of triethylamine at 0° C.; step [g] can be conducted by heating using sodium azide in hexamethylphosphamide (HMPA); step [h] can be performed by using lithium aluminium hydride in diethyl ether; step [i] can be performed by reacting using trifluoroacetic anhydride in methylene chloride in the presence of pyridine at 0° C.; step [j] can be conducted by reacting in methanol in the presence of p-toluenesulfonic acid; step [k] can be conducted by using a sulfur trioxidepyridine complex in dimethylsulfoxide in the presence of triethylamine; and step [l] can be conducted by performing Wittig reaction using an ylide of a phosphonium compound of the general formula:

$(R^8)_3P^{\oplus}-CH_2-D-COOH.X^{\ominus}$   XVII (wherein D represents the group —$(CH_2)_m$—, in which m is as hereinbefore defined, or a phenylene group of the formula

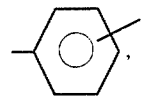

$R^8$ represents a phenyl group unsubstituted or substituted by an alkyl group of 1 to 4 carbon atoms, preferable a phenyl group, or an alkyl group of 1 to 6 carbon atoms, preferable a butyl or hexyl group, or a cyclohexyl group, and X is as hereinbefore defined) in dimethylsulfoxide and, if desired, performing esterification using an esterification method hereinafter described, and further, if desired, subjecting the product to hydrogenation in a lower alkanol such as methanol or ethanol in the presence of a hydrogenating catalyst such as palladium on carbon, palladium black or platinum dioxide. The product wherein B represents a group of the formula

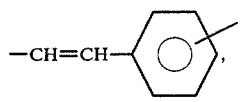

thus obtained, is a mixture of isomers in which the double bond is in trans and cis. If desired, the mixture may be separated by column, thin layer or high-speed liquid chromatography on silica gel to give each of the isomers. The ylide can be obtained by reacting a compound of the general formula XVII in the presence of an appropriate base, such as butyl lithium, lithium diisopropylamide, dimsyl sodium, sodium methoxide, potassium tert-butoxide, triethylamine, preferably dimsyl sodium. The phosphonium compounds XVII are well known and can be prepared by methods known per se. Step [m] can be carried out by subjecting to saponification described hereinafter and, if desired, subjecting to esterification described hereinafter.

Compounds of general formula XIII in Scheme A wherein two $R^2$ both represent hydrogen atoms can be obtained by subjecting 2-oxonorpinane as disclosed in Chem. Ber., 100, 3627 (1967) to Wittig reaction using a method as described in J. Org. Chem., 28, 1128 (1963). Compounds of general formula XIII wherein two $R^2$ both represent methyl groups is well known as β-pinene.

Starting materials of the general formula VII, wherein A represents the group —$CH_2$—O—$(CH_2)_m$—, in which m is as hereinbefore defined, i.e. compounds of the general formula:

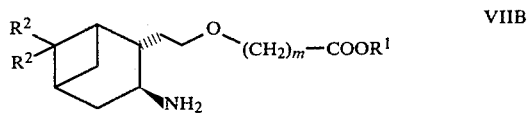   VIIB (wherein the various symbols are as hereinbefore defined) may be prepared from a compound of the general formula:

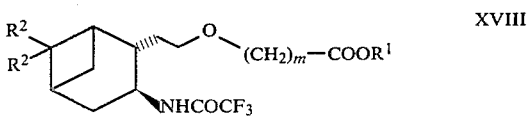   XVIII (wherein the various symbols are as hereinbefore defined) by methods hereinbefore described for step [m] in Scheme A.

Compounds of the general formula XVIII may be prepared by oxidation of compounds of the general formula:

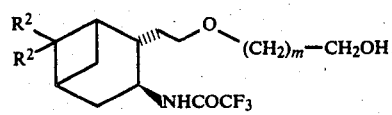   XIX (wherein the various symbols are as hereinbefore defined) using an appropriate oxidazing agent, e.g. Jones' reagent and, if desired, esterification described hereinafter.

Compounds of the general formula XIX may be prepared by the series of reactions depicted in Scheme A, i.e. step [c]→[d]→[e]→[f]→[g]→[h]→[i]→[j], but replacing the compounds of general formula XV by compounds of the general formula:

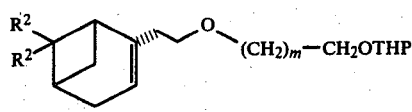   XX (wherein the various symbols are as hereinbefore defined).

Compounds of the general formula XX may be prepared by reacting compounds of general formula XIV with compounds of the general formula:

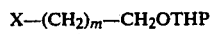   XXI

X—(CH$_2$)$_m$—CH$_2$OTHP (wherein the various symbols are as hereinbefore defined) in dimethyl sulphoxide in the presence of sodium hydride.

Compounds of the general formula VA wherein A represents other than a group of the formula —CH$_2$—O—(CH$_2$)$_m$—, i.e. compounds of the general formula:

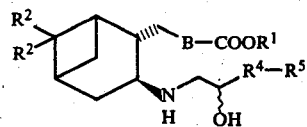   VC (wherein the various symbols are as hereinbefore defined), may also be prepared from compounds of the general formula XVI by the series of reactions depicted schematically below in Scheme B, wherein the various symbols are as hereinbefore defined.

Scheme B

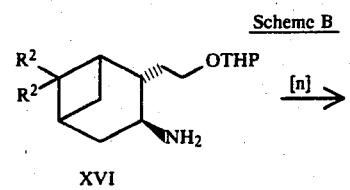

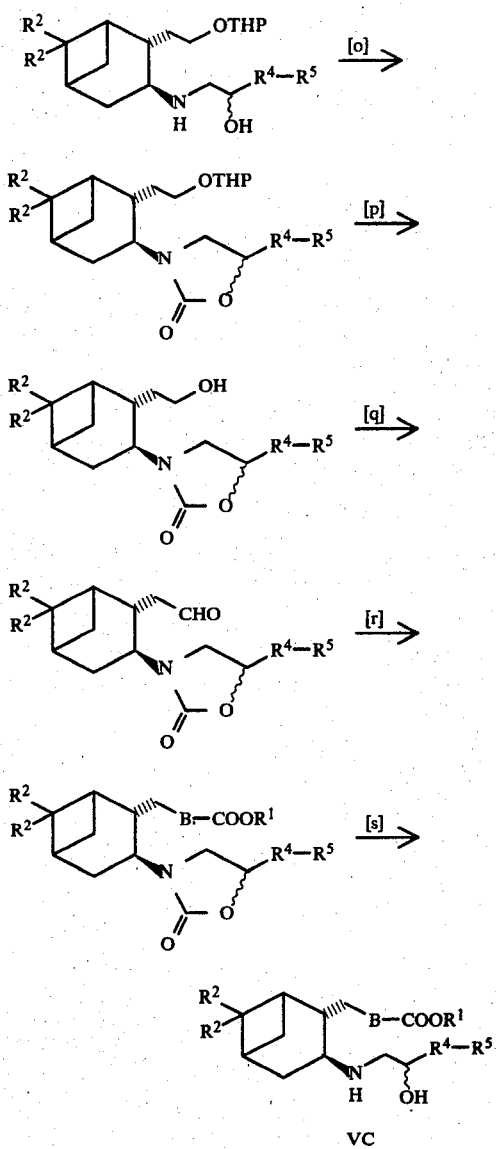

In the Scheme B, step [n] can be carried out by methods hereinbefore described for the conversion of compounds of the general formula VII to those of the general formula VA. Step [o] can be carried out by methods as described in J. Amer. Chem. Soc., 73, 2390 (1951), for example, by reacting with ethyl chloroformate in an inert organic solvent such as toluene in the presence of a base at a temperature from 0° C. to a refluxing temperature of the solvent. Steps [p], [q], [r] and [s] can be conducted by methods hereinbefore described for steps [j], [k], [l] and [m] in Scheme A, respectively.

Carboxylic acids of the general formula V wherein R$^1$ represents a hydrogen atom and the other symbols are as hereinbefore defined can be obtained by saposifying the corresponding esters of the general formula V wherein R$^1$ represents a group other than hydrogen atom and the other symbols are as hereinbefore defined by methods known per se. For example, methods for saponification are disclosed in Compendium of Organic Synthetic Methods, vol. 1 (1971), vol 2 (1974) and vol.

3 (1977), Section 23 published by John Wiley & Sons, Inc., U.S.A. Saponification is suitable conducted in the presence or absence of a water-miscible solvent, such as ethers, e.g. dioxane or tetrahydrofuran, or alkanols of 1 to 4 carbon atoms, e.g. methanol or ethanol, at a temperature from $-10°$ C. to $100°$ C., preferably at room temperature, using an aqueous solution of a hydroxide or a carbonate of an alkali metal, e.g. sodium, potassium or lithium, or an alkaline earth metal, e.g. calcium or barium, or conducted in an anhydrous alkanol of 1 to 4 carbon atoms, e.g. absolute methanol or absolute ethanol, at a temperature from $-10°$ C. to $100°$ C., preferably at room temperature, using a hydroxide or carbonate of an alkali metal, e.g. sodium, potassium or lithimm.

Esters of the general formula V wherein $R^1$ represents a group other than a hydrogen atom and the other symbols are as hereinbefore defined can be obtained by esterifying the corresponding carboxylic acids of the general formula V wherein $R^1$ represents a hydrogen atom and the other symbols are as hereinbefore defined by methods known per se. For example, the esterification is conducted using (1) a process of using a diazoalkane, or
(2) a process of using N,N-dimethylformamide-dialkylacetal [cf. Helv. Chim. Acta, 48, 1746 (1965)].

The esterification using a diazoalkane is conducted using the corresponding acid and an appropriate diazoalkane in an inert organic solvent, such as diethyl ether, ethyl acetate, methylene chloride, acetone, methanol or a mixed solvent of two or more of them, at a temperature, of from room temperature to $-10°$ C., preferably $0°$ C.

The esterification using N,N-dimethylformamide-dialkylacetal is conducted using the corresponding acid and an appropriate N,N-dimethylformamide-dialkylacetal, such as N,N-dimethylformamide-dimethylacetal, in anhydrous benzene at a temperature of from room temperature to $0°$ C.

Cyclodextrin clathrates of the 11a-carbathrombanoic acid analogues of the general formula V can be obtained by using $\alpha$-, $\beta$- or $\gamma$-cyclodextrin or a mixture thereof employing a method as described in our British Pat. Nos. 1,351,238 and 1,419,221. By convering into a cyclodextrin clathrate, the stability of the 11a-carbathrombanoic acid analogues of the general formula V can be increased.

Acids of the general formula V wherein $R^1$ represents a hydrogen atom are converted into salts by methods known per se. The salts are preferable non-toxic salts. The non-toxic salts herein referred mean salts of cations such that it is relatively innoxious to animal tissue and that the effective pharmacological properties of the compounds of the general formula V are not impaired by side effects resulting from the cations when used in an amount required for the treatment. It is preferable that the salts are water-soluble. Suitable salts include, for example, a salt of an alkali metal such as sodium or potassium, a salt of an alkaline earth metal such as calcium or magnesium, an ammonium salt and a pharmaceutically acceptable (non-toxic) amine salt. Amines suitable for forming such a salt with a carboxylic acid are well known, and include, for example, those amines which are theoretically obtained by substituting one or more hydrogen atoms of ammonia by other groups. These groups, which may be the same or different with each other when one or more hydrogen atoms are substituted, are selected from, for example, alkyl groups of 1 to 6 carbon atoms and hydroxyalkyl groups of 2 or 3 carbon atoms. Suitable non-toxic amine salts include salts of a tetraalkylammonium, such as tetramethylammonium and salts of an organic amine, such as methylamine, dimethylamine, cyclopentylamine, benzylamine, phenethylamine, piperidine, monoethanolamine, diethanolamine, lysine, and alginine.

Salts can be obtained from the acids of the general formula V by methods known per se, for example, by reacting the acid of the general formula V and a suitable base, such as a hydroxide or carbonate of an alkali metal or alkaline earth metal, ammonium hydroxide, ammonia or an organic amine in theoretical amounts in an appropriate solvent. The salts can be isolated by lyophilisation of the solution, or by filtration if the salts are sufficiently insoluble in the reaction solvent, or, if necessary by removing part of the solvent followed by filtration.

The compounds of the present invention of the general formula V have an antagonistic activity on thromboxane $A_2$, i.e. inhibitory activity on platelet aggregation and inhibitory activity on aorta contraction, and are, therefore, useful for prevention and treatment of inflammation, hypertension, thrombus, cerebral apoplexy, asthma, cardiac infarction, angina pectoris, cerebral infarction and death by acute cardiac disorders in mammals including human, in particularly human, which are considered to be induced by thromboxane $A_2$. For example, in standard laboratory test, $(5Z,15\beta)$-9,11-methano-10,10-dimethyl-13-aza-15-hydroxy-11a-carbathromb-5-enoic acid, $(5Z,15\alpha)$-9,11-methano-10,10-dimethyl-13-aza-15-hydroxy-11a-carbathromb-5-enoic acid, $(5Z,15\beta)$-9,11-methano-10,10-dimethyl-13-aza-15-hydroxy-16-phenoxy-17,18,19,20-tetranor-11a-carbathromb-5-enoic acid, $(5Z,15\alpha)$-9,11-methano-10,10-dimethyl-13-aza-15-hydroxy-16-phenoxy-17,18,19,20-tetranor-11a-carbathromb-5-enoic aicd, $(5Z,15\beta)$-9,11-methano-10,10-dimethyl-13-aza-15-hydroxy-16-phenylthio-17,18,19,20-tetranor-11a-carbathromb-5-enoic acid and $(5Z,15\alpha)$-9,11-methano-10,10-dimethyl-13-aza-15-hydroxy-16-phenylthio-17,18,19,20-tetranor-11a-carbathromb-5-enoic acid produce (i) a 50% inhibition of 11-methanoepoxy-PGH$_2$-induced blood platelet aggregation [cf. Tetrahedron Letters, 1957 (1975)] in platelet-rich plasma of human at the concentration of 0.69, 0.92, 2.98, 14.36, 0.24 and 0.67 $\mu$M, respectively, and produce (ii) a 50% inhibition of (9,11),(11,12)-dimethanothromboxane $A_2$-induced aorta contraction [cf. Tetrahedron Letters, 3661 (1979)] in rats at the concentrations of 5, 5, 1, 2, 1 and 0.9 $\mu$M, respectively The present invention includes within its scope pharmaceutical compositions which comprise at least one new therapeutically useful compound of the general formula V, or cyclodextrin clathrate thereof, or, when $R^1$ in formula V represents a hydrogen atom, non-toxic salt thereof, together with a pharmaceutical carrier or coating. In clinical practice the new compounds of the general formula V will normally be administered orally, rectally or parenterally.

Solid compositions for oral administration include compressed tablets, pills, dispersible powders and granules. In such solid compositions one or more of the active compounds is, or are, admixed with at least one inert diluent such as calcium carbonate, potato starch, dextrin, alginic acid, lactose, mannitol, glucose or cacao butter. The compositions may also comprise, as is normal practice, additional substances other than inert diluents, e.g. lubricating agents such as magnesium stearate. The tablets or pills may, if desired, be coated and made into sugar-coated, gelatin-coated, enteric-coated or film-coated tablets or pills, or tablets or pills coated with two or more layers.

Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants such as wetting and suspending agents, and sweetening, flavouring, perfuming and preserving agents.

The compositions according to the invention for oral administration, also include capsules of absorbable material such as gelatin containing one or more of the active substances with or without the addition of diluents or excipients.

Solid compositions for intrarectal administration include suppositories formulated in manner known per se and containing one or more of the active substances.

Preparations according to the invention for parenteral administration include sterile aqueous or non-aqueous solutions, suspensions or emulsions. Examples of non-aqueous solvents or suspending media are propylene glycol, polyethylene glycol, ethanol, vegetable oils such as olive oil, and injectable organic esters such as ethyl oleate and sorbitan esters. These compositions may also include adjuvants such as preserving, wetting, emulsifying and dispersing agents. They may be sterilised, for example by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varried, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dosage employed depends upon the desired therapeutic effect, the poute of administration, the duration of the treatment, and the age and body weight of the patient.

In the adult, each dose per person is generally between 0.1 mg and 1 g by oral, intrarectal, intravenous, intramuscular or subcutaneous administration in the prevention and treatment of inflammation, hypertension, thrombus, cerebral apoplexy, asthma, cardiac infarction, angina pectoris, cerebral infarction and death by acute cardiac disorders. The dosage will normally be administered once or several times per day.

Preferred compounds of the present invention are as follows: (5Z,15ξ)-9,11-methano-10,10-dimethyl-13-aza-15-hydroxy-11a-carbathromb-5-enoic acid, (15ξ)-9,11-methano-10,10-dimethyl-13-aza-15-hydroxy-11a-carbathrombanoic acid, (5Z,15ξ)-9,11-methano-13-aza-15-hydroxy-11a-carbathromb-5-enoic acid, (15ξ)-9,11-methano-13-aza-15-hydroxy-11a-carbathrombanoic acid, (5Z,15ξ)-9,11-methano-10,10-dimethyl-13-aza-15-hydroxy-20-methyl-11a-carbathromb-5-enoic acid, (15ξ)-9,11-methano-10,10-dimethyl-13-aza-15-hydroxy-20-methyl-11a-carbathrombanoic acid, (5Z,15ξ)-9,11-methano-13-aza-15-hydroxy-20-methyl-11a-carbathromb-5-enoic acid, (15ξ)-9,11-methano-13-aza-15-hydroxy-20-methyl-11a-carbathrombanoic acid, (5Z,15ξ)-9,11-methano-10,10-dimethyl-13-aza-15-hydroxy-20-ethyl-11a-carbathromb-5-enoic acid, (15ξ)-9,11-methano-10,10-dimethyl-13-aza-15-hydroxy-20-ethyl-11a-carbathrombanoic acid, (5Z,15ξ)-9,11-methano-13-aza-15-hydroxy-20-ethyl-11a-carbathromb-5-enoic acid, (15ξ)-9,11-methano-13-aza-15-hydroxy-20-ethyl-11a-carbathrombanoic acid, (5Z,15ξ)-9,11-methano-10,10-dimethyl-13-aza-15-hydroxy-20-propyl-11a-carbathromb-5-enoic acid, (15ξ)-9,11-methano-10,10-dimethyl-13-aza-15-hydroxy-20-propyl-11a-carbathrombanoic acid, (5Z,15ξ)-9,11-methano-13-aza-15-hydroxy-20-propyl-11a-carbathromb-5-enoic acid, (15ξ)-9,11-methano-13-aza-15-hydroxy-20-propyl-11a-carbathrombanoic acid, (5Z,15ξ,16ξ)-9,11-methano-10,10,16-trimethyl-13-aza-15-hydroxy-11a-carbathromb-5-enoic acid, (15ξ,16ξ)-9,11-methano-10,10,16-trimethyl-13-aza-15-hydroxy-11a-carbathrombanoic acid, (5Z,15ξ,16ξ)-9,11-methano-13-aza-15-hydroxy-16-methyl-11a-carbathromb-5-enoic acid, (15ξ,16ξ)-9,11-methano-13-aza-15-hydroxy-16-methyl-11a-carbathrombanoic acid, (5Z,15ξ,16ξ)-9,11-methano-10,10,16,20-tetramethyl-13-aza-15-hydroxy-11a-carbathromb-5-enoic acid, (15ξ,16ξ)-9,11-methano-10,10,16,20-tetramethyl-13-aza-15-hydroxy-11a-carbathrombanoic acid, (5Z,15ξ,16ξ)-9,11-methano-13-aza-15-hydroxy-16,20-dimethyl-11a-carbathromb-5-enoic acid, (15ξ,16ξ)-9,11-methano-13-aza-15-hydroxy-16,20-dimethyl-11a-carbathrombanoic acid, (5Z,15ξ,16ξ)-9,11-methano-10,10,16-trimethyl-13-aza-15-hydroxy-20-ethyl-11a-carbathromb-5-enoic acid, (15ξ,16ξ)-9,11-methano-10,10,16-trimethyl-13-aza-15-hydroxy-20-ethyl-11a-carbathrombanoic acid, (5Z,15ξ,16ξ)-9,11-methano-13-aza-15-hydroxy-20-ethyl-11a-carbathromb-5-enoic acid, (15ξ,16ξ)-9,11-methano-13-aza-15-hydroxy-20-ethyl-11a-carbathrombanoic acid, (5Z,15ξ,17ξ)-9,11-methano-10,10,17-trimethyl-13-aza-15-hydroxy-11a-carbathromb-5-enoic acid, (15ξ,17ξ)-9,11-methano-10,10,17-trimethyl-13-aza-15-hydroxy-11a-carbathrombanoic acid, (5Z,15ξ,17ξ)-9,11-methano-13-aza-15-hydroxy-17-methyl-11a-carbathromb-5-enoic acid, (15ξ,17ξ)-9,11-methano-13-aza-15-hydroxy-17-methyl-11a-carbathrombanoic acid, (5ξ,15ξ,17ξ)-9,11-methano-10,10,17,20-tetramethyl-13-aza-15-hydroxy-11a-carbathromb-5-enoic acid, (15ξ,17ξ)-9,11-methano-10,10,17,20-tetramethyl-13-aza-15-hydroxy-11a-carbathrombanoic acid, (5Z,15ξ,17ξ)-9,11-methano-13-aza-15-hydroxy-17,20-dimethyl-11a-carbathromb-5-enoic acid, (15ξ,17ξ)-9,11-methano-13-aza-15-hydroxy-17,20-dimethyl-11a-carbathrombanoic acid, (5Z,15ξ,17ξ)-9,11-methano-10,10,17-trimethyl-13-aza-15-hydroxy-20-ethyl-11a-carbathromb-5-enoic acid, (15ξ,17ξ)-9,11-methano-10,10,17-trimethyl-13-aza-15-hydroxy-20-ethyl-11a-carbathrombanoic acid, (5Z,15ξ,17ξ)-9,11-methano-13-aza-15-hydroxy-17-methyl-20-ethyl-11a-carbathromb-5-enoic acid, (15ξ,17ξ)-9,11-methano-13-aza-15-hydroxy-17-methyl-20-ethyl-11a-carbathrombanoic acid, (5Z,15ξ)-9,11-methano-10,10-dimethyl-13-aza-15-hydroxy-15-(1-propylcyclobutyl)-16,17,18,19,20-pentanor-11a-carbathromb-5-enoic acid, (15ξ)-9,11-methano-10,10-dimethyl-13-aza-15-hydroxy-15-(1-propylcyclobutyl)-16,17,18,19,20-pentanor-11a-carbathrombanoic acid, (5Z,15ξ)-9,11-methano-13-aza-15-hydroxy-15-(1-propylcyclobutyl)-16,17,18,19,20-pentanor-11a-carbathromb-5-enoic acid, (15ξ)-9,11-methano-13-aza-15- hydroxy-15-(1-propylcyclobutyl)-16,17,18,19,20-pentanor-11a-carbathrombanoic acid, (5Z,15ξ)-9,11-methano-10,10-dimethyl-13-aza-15-hydroxy-15-(1-butylcyclobutyl)-16,17,18,19,20-pentanor-11a-carbathromb-5-enoic acid, (15ξ)-9,11-methano-10,10-dimethyl-13-aza-15-hydroxy-15-(1-butylcyclobutyl)-16,17,18,19,20-pentanor-11a-carbathrombanoic acid, (5Z,15ξ)-9,11-methano-13-aza-15-hydroxy-15-(1-butylcyclobutyl)-16,17,18,19,20-petanor-11a-carbathromb-5-enoic acid, (15ξ)-9,11-methano-13-aza-15-hydroxy-15-(1-butylcyclobutyl)-16,17,18,19,20-pentanor-11a-carbathrombanoic acid, (5Z,15ξ)-9,11-methano-10,10-dimethyl-13-aza-15-hydroxy-15-(1-pentylcyclobutyl)-16,17,18,19,20-pentanor-11a-carbathromb-5-enoic acid, (15ξ)-9,11-methano-10,10-dimethyl-13-aza-15-hydroxy-15-(1-pentylcyclobutyl)-16,17,18,19,20-pentanor-11a-carbathrombanoic acid, (5Z,15ξ)-9,11-methano-13-aza-15-hydroxy-15-(1-pentylcyclobutyl)-16,17,18,19,20-pentanor-11a-carbathromb-5-enoic acid, (15ξ)-9,11-methano-13-aza-15-hydroxy-15(1-pentylcyclobutyl)-16,17,18,19,20-pentanor-11a-carbathrombanoic acid, (5Z,15ξ)-9,11-methano-10,10-dimethyl-13-aza-15-hydroxy-15-(1-hexylcyclobutyl)-16,17,18,19,20-pentanor-11a-carbathromb-5-enoic acid, (15ξ)-9,11-methano-10,10-dimethyl-13-aza-15-hydroxy-15-(1-hexylcyclobutyl)-16,17,18,19,20-pentanor-11a-carbathrombanoic acid, (5Z,15ξ)-9,11-methano-13-aza-15-hydroxy-15-(1-hexylcyclobutyl)-16,17,18,19,20-pentanor-11a-carbathromb-5-enoic acid, (15ξ)-9,11-methano-13-aza-15-hydroxy-15(1-hexylcyclobutyl)-16,17,18,19,20-pentanor-11a-carbathrombanoic acid, (5Z,15ξ)-9,11-methano-10,10-dimethyl-13-aza-15-hydroxy-15-cyclopentyl-16,17,18,19,20-pentanor-11a-carbathromb-5-enoic acid, (15ξ)-9,11-methano-10,10-dimethyl-13-aza-15-hydroxy-15-cyclopentyl-16,17,18,19,20-pentanor-11a-carbathrombanoic acid, (5Z,15ξ)-9,11-methano-13-aza-15-hydroxy-15-cyclopentyl-16,17,18,19,20-pentanor-11a-carbathromb-5-enoic acid, (15ξ)-9,11-methano-13-aza-15-hydroxy-15-cyclopentyl-16,17,18,19,20-pentanor-11a-carbathrombanoic acid, (5Z,15ξ)-9,11-methano-10,10-dimethyl-13-aza-15-hydroxy-15-(3-methylcyclopentyl)-16,17,18,19,20-pentanor-11a-carbathromb-5-enoic acid, (15ξ)-9,11-methano-10,10-dimethyl-13-aza-15-hydroxy-15-(3-methylcyclopentyl)-16,17,18,19,20-pentanor-11a-carbathrombanoic acid, (5Z,15ξ)-9,11-methano-13-aza-15-hydroxy-15-(3-methylcyclopentyl)-16,17,18,19,20-pentanor-11a-carbathromb-5-enoic acid, (15ξ)-9,11-methano-13-aza-15-hydroxy-15(3-methylcyclopentyl)-16,17,18,19,20-pentanor-11a-carbathrombanoic acid, (5Z,15ξ)-9,11-methano-10,10-dimethyl-13-aza-15-hydroxy-15-(3-ethylcyclopentyl)-16,17,18,19,20-pentanor-11a-carbathromb-5-enoic acid, (15ξ)-9,11-methano-10,10-dimethyl-13-aza-15-hydroxy-15-(3-ethylcyclopentyl)-16,17,18,19,20-pentanor-11a-carbathrombanoic acid, (5Z,15ξ)-9,11-methano-13-aza-15-hydroxy-15-(3-ethylcyclopentyl)-16,17,18,19,20-pentanor-11a-carbathromb-5-enoic acid, (15ξ)-9,11-methano-13-aza-15-hydroxy-15-(3-ethylcyclopentyl)-16,17,18,19,20-pentanor-11a-carbathrombanoic acid, (5Z,15ξ)-9,11-methano-10,10-dimethyl-13-aza-15-hydroxy-15-(3-propylcyclopentyl)-16,17,18,19,20-pentanor-11a-carbathromb-5-enoic acid, (15ξ)-9,11-methano-10,10-dimethyl-13-aza-15-hydroxy-15-(3-propylcyclopentyl)-16,17,18,19,20-pentanor-11a-carbathrombanoic acid, (5Z,15ξ)-9,11-methano-13-aza-15-hydroxy-15-(3-propylcyclopentyl)-16,17,18,19,20-pentanor-11a-carbathromb-5-enoic acid, (15ξ)-9,11-methano-13-aza-15-hydroxy-15-(3-propylcyclopentyl)-16,17,18,19,20-pentanor-11a-carbathrombanoic acid, (5Z,15ξ)-9,11-methano-10,10-dimethyl-13-aza-15-hydroxy-15-(3-butylcyclopentyl)-16,17,18,19,20-pentanor-11a-carbathromb-5-enoic acid, (15ξ)-9,11-methano-10,10-dimethyl-13-aza-15-hydroxy-15-(3-butylcyclopentyl)-16,17,18,19,20-pentanor-11a-carbathrombanoic acid, (5Z,15ξ)-9,11-methano-13-aza-15-hydroxy-15-(3-butylcyclopentyl)-16,17,18,19,20-pentanor-11a-carbathromb-5-enoic acid, (15ξ)-9,11-methano-13-aza-15-hydroxy-15-(3-butylcyclopentyl)-16,17,18,19,20-pentanor-11a-carbathrombanoic acid, (5Z,15ξ)-9,11-methano-10,10-dimethyl-13-aza-15-hydroxy-15-cyclohexyl-16,17,18,19,20-pentanor-11a-carbathromb-5-enoic acid, (15ξ)-9,11-methano-10,10-dimethyl-13-aza-15-hydroxy-15-cyclohexyl-16,17,18,19,20-pentanor-11a-carbathrombanoic acid, (5Z,15ξ)-9,11-methano-13-aza-15-hydroxy-15-cyclohexyl-16,17,18,19,20-pentanor-11a-carbathromb-5-enoic acid, (15ξ)-9,11-methano-13-aza-15-hydroxy-15-cyclohexyl-16,17,18,19,20-pentanor-11a-carbathrombanoic acid, (5Z,15ξ)-9,11-methano-10,10-dimethyl-13-aza-15-hydroxy-15-(3-methylcyclohexy)-16,17,18,19,20-pentanor-11a-carbathromb-5-enoic acid, (15ξ)-9,11-methano-10,10-dimethyl-13-aza-15-hydroxy-15-(3-methylcyclohexyl)-16,17,18,19,20-pentanor-11a-carbathrombanoic acid, (5Z,15ξ)-9,11-methano-13-aza-15-hydroxy-15-(3-methylcyclohexyl)-16,17,18,19,20-pentanor-11a-carbathromb-5-enoic acid, (15ξ)-9,11-methano-13-aza-15-hydroxy-15-(3-methylcyclohexyl)-16,17,18,19,20-pentanor-11a-carbathrombanoic acid, (5Z,15ξ)-9,11-methano-10,10-dimethyl-13-aza-15-hydroxy-15-(3-ethylcyclohexyl)-16,17,18,19,20-pentanor-11a-carbathromb-5-enoic acid, (15ξ)-9,11-methano-10,10-dimethyl-13-aza-15-hydroxy-15-(3-ethylcyclohexyl)-16,17,18,19,20-pentanor-11a-carbathrombanoic acid, (5Z,15ξ)-9,11-methano-13-aza-15-hydroxy-15-(3-ethylcyclohexyl)-16,17,18,19,20-pentanor-11a-carbathromb-5-enoic acid, (15ξ)-9,11-methano-13-aza-15-hydroxy-15-(3-ethylcyclohexyl)-16,17,18,19,20-pentanor-11a-carbathrombanoic acid, (5Z,15ξ)-9,11-methano-10,10-dimethyl-13-aza-15-hydroxyl-15-(3-propylcyclohexyl)-16,17,18,19,20-pentanor-11a-carbathromb-5-enoic acid, (15ξ)-9,11-methano-10,10-dimethyl-13-aza-15-hydroxy-15-(3-propylcyclohexyl)-16,17,18,19,20-pentanor-11a-carba-thrombanoic acid, (5Z,15ξ)-9,11-methano-13-aza-15-hydroxy-15-(3-propyl-cyclohexyl)-16,17,18,19,20-pentanor-11a-carbathromb-5-enoic acid, (15ξ)-9,11-methano-13-aza-15-hydroxy-(3-propylcyclohexyl)-16,17,18,19,20-pentanor-11a-carbathrombanoic acid, (5Z,15ξ)-9,11-methano-10,10-dimethyl-13-aza-15-hydroxy-15-(3-butylcyclohexyl)-16,17,18,19,20-pentanor-11a-carbathromb-5-enoic acid, (15ξ)-9,11-methano-10,10-dimethyl-13-aza-15-hydroxy-15-(3-butylcyclohexyl)-16,17,18,19,20-pentanor-11a-carbathrombanoic acid, (5Z,15ξ)-9,11-methano-13-aza-15-hydroxy-15-(3-butylcyclohexyl)-16,17,18,19,20-pentanor-11a-carbathromb-5-enoic acid, (15ξ)-9,11-methano-13-aza-15-hydroxy-15-(3-butylcyclohexyl)-16,17,18,19,20-pentanor-11a-carbathrombanoic acid, (5Z,15ξ)-9,11-methano-10,10-dimethyl-13-aza-15-hydroxy-15-(4-methylcyclohexyl)-16,17,18,19,20-pentanor-11a-carbathromb-5-enoic acid, (15ξ)-9,11-methano-10,10-dimethyl-13-aza-15-hydroxy-15-(4-methylcyclohexyl)-16,17,18,19,20-pentanor-11a-carbathrombanoic acid, (5Z,15ξ)-9,11-methano-13-aza-15-hydroxy-15(4-methylcyclohexyl)-16,17,18,19,20-pentanor-11a-carbathromb-5-enoic acid, (15ξ)-9,11-methano-13-aza-hydroxy-15-(4-methylcyclohexyl)-

16,17,18,19,20-pentanor-11a-carbathrombanoic acid, (5Z,15ξ)-9,11-methano-10,10-dimethyl-13-aza-15-hydroxy-15-(4-ethylcyclohexyl)-16,17,18,19,20-pentanor-11a-carbathromb-5-enoic acid, (15ξ)-9,11-methano-10,10-dimethyl-13-aza-15-hydroxy-15-(4-ethylcyclohexyl)-16,17,18,19,20-pentanor-11a-carbathrombanoic acid, (5Z,15ξ)-9,11-methano-13-aza-15-hydroxy-15-(4-ethylcyclohexyl)-16,17,18,19,20-pentanor-11a-carbathomb-5-enoic acid, (15ξ)-9,11-methano-13-aza-15-hydroxy-15-(4-ethylcyclohexyl)-16,17,18,19,20-pentanor-11a-carbathrombanoic acid, (5Z,15ξ)-9,11-methano-10,10-dimethyl-13-aza-15-hydroxy-15-(4-propylcylohexyl)-16,17,18,19,20-pentanor-11a-carbathromb-5-enoic acid, (15ξ)-9,11-methano-10,10-dimethyl-13-aza-15-hydroxy-15-(4-propylcyclohexyl)-16,17,18,19,20-pentanor-11a-carbathrombanoic acid, (5Z,15ξ)-9,11-methano-13-aza-15-hydroxy-15-(4-propylcyclohexyl)-16,17,18,19,20-pentanor-11a-carbathromb-5-enoic acid, (15ξ)-9,11-methano-13-aza-15-hydroxy-15-(4-propylcyclohexyl)-16,17,18,19,20-pentanor-11a-carbathrombanoic acid, (5Z,15ξ)-9,11-methano-10,10-dimethyl-13-aza-15-hydroxy-15-cycloheptyl-16,17,18,19,20-pentanor-11a-carbathromb-5-enoic acid, (15ξ)-9,11-methano-10,10-dimethyl-13-aza-15-hydroxy-15-cycloheptyl-16,17,18,19,20-pentanor-11-carbathrombanoic acid, (5Z,15ξ)-9,11-methano-13-aza-15-hydroxy-15-cycloheptyl-16,17,18,19,20-pentanor-11a-carbathromb-5-enoic acid, (15ξ)-9,11-methano-13-aza-15-hydroxy-15-cycloheptyl-16,17,18,19,20-pentanor-11a-carbathrombanoic acid, (5Z,15ξ)-9,11-methano-10,10-dimethyl-13-aza-15-hydroxy-16-cyclopentyl-17,18,19,20-tetranor-11a-carbathromb-5-enoic acid, (15ξ)-9,11-methano-10,10-dimethyl-13-aza-15-hydroxy-16-cyclopentyl-17,18,19,20-tetranor-11a-carbathrombanoic acid, (5Z,15ξ)-9,11-methano-13-aza-15-hydroxy-16-cyclopentyl-17,18,19,20-tetranor-11a-carbathromb-5-enoic acid, (15ξ)-9,11-methano-13-aza-15-hydroxy-16-cyclopentyl-17,18,19,20-tetranor-11a-carbathrombanoic acid, (5Z,15ξ)-9,11-methano-10,10-dimethyl-13-aza-15-hydroxy-16-cyclo-hexyl-17,18,19,20-tetranor-11a-carbathromb-5-enoic acid, (15ξ)-9,11-methano-10,10-dimethyl-13-aza-15-hydroxy-16-cyclohexyl-17,18,19,20-tetranor-11a-carbathrombanoic acid, (5Z,15ξ)-9,11-methano-13-aza-15-hydroxy-16-cyclohexyl-17,18,19,20-tetranor-11a-carbathromb-5-enoic acid, (15ξ)-9,11-methano-13-aza-15-hydroxy-16-cyclohexyl-17,18,19,20-tetranor-11a-carbathrombanoic acid, (5Z,15ξ)-9,11-methano-10,10-dimethyl-13-aza-15-hydroxy-16-phenoxy-17,18,19,20-tetranor-11a-carbathromb-5-enoic acid, (5ξ)-9,11-methano-10,10-dimethyl-13-aza-15-hydroxy-16-phenox-17,18,19,20-tetranor-11a-carbathrombanoic acid, (5Z,15ξ)-9,11-methano-13-aza-15-hydroxy-16-phenoxy-17,18,19,20-tetranor-11a-carbathromb-5-enoic acid, (15ξ)-9,11-methano-13-aza-15-hydroxy-16-phenoxy-17,18,19,20-tetranor-11a-carbathrombanoic acid, (5Z,15ξ)-9,11-methano-10,10-dimethyl-13-aza-15-hydroxy-16-(3-methyphenoxy)-17,18,19,20-tetranor-11a-carbathromb-5-enoic acid, (15ξ)-9,11-methano-10,10-dimethyl-13-aza-15-hydroxy-16-(3-methylphenoxy)-17,18,19,20-tetranor-11a-carbathrombanoic acid, (5Z,15ξ)-9,11-methano-13-aza-15-hydroxy-16-(3-methylphenoxy)-17,18,19,20-tetranor-11a-carbathromb-5-enoic acid, (15ξ)-9,11-methano-13-aza-15-hydroxy-16-(3-methylphenoxy)-17,18,19,20-tetranor-11a-carbathrombanoic acid, (5Z,15ξ)-9,11-methano-10,10-dimethyl-13-aza-15-hydroxy-16-(3-ethylphenoxy)-17,18,19,20-tetranor-11a-carbathromb-5-enoic acid, (15ξ)-9,11-methano-10,10-dimethyl-13-aza-15-hydroxy-16-(3-ethylphenoxy)-17,18,19,20-tetranor-11a-carbathrombanoic acid, (5Z,15ξ)-9,11-methano-13-aza-hydroxy-16-(3-ethylphenoxy)-17,18,19,20-tetranor-11a-carbathromb-5-enoic acid, (15ξ)-9,11-methano-13-aza-15-hydroxy-16-(3-ethylphenoxy)-17,18,19,20-tetranor-11a-carbathrombanoic acid, (5Z,15ξ)-9,11-methano-10,10-dimethyl-13-aza-15-hydroxy-16-(propylphenoxy)-17,18,19,20-tetranor-11a-carbathromb-5-enoic acid, (15ξ)-9,11-methano-10,10-dimethyl-13-aza-15-hydroxy-16-(3-propylphenoxy)-17,18,19,20-tetranor-11a-carbathrombanoic acid, (5Z,15ξ)-9,11-methano-13-aza-15-hydroxy-16-(3-propylphenoxy)-17,18,19,20-tetranor-11a-carbathromb-5-enoic acid, (15ξ)-9,11-methano-13-aza-15-hydroxy-16-(3-propylphenoxy)-17,18,19,20-tetranor-11a-carbathrombanoic acid, (5Z,15ξ)-9,11-methano-10,10-dimethyl-13-aza-15-hydroxy-16-(3-tert-butylphenoxy)-17,18,19,20-tetranor-11a-carbathromb-5-enoic acid, (15ξ)-9,11-methano-10,10-dimethyl-13-aza-15-hydroxy-16-(3-tert-butylphenoxy)-17,18,19,20-tetranor-11a-carbathrombanoic acid, (5Z,15ξ)-9,11-methano-13-aza-15-hydroxy-16-(3-tert-butylphenoxy)-17,18,19,20-tetranor-11a-carbathromb-5-enoic acid, (15ξ)-9,11-methano-13-aza-15-hydroxy-16-(3-tert-butylphenoxy)-17,18,19,20-tetranor-11a-carbathrombanoic acid, (5Z,15ξ)-9,11-methano-10,10-dimethyl-13-aza-15-hydroxy-16-(3-chlorophenoxy)-17,18,19,20-tetranor-11a-carbathromb-5-enoic acid, (15ξ)-9,11-methano-10,10-dimethyl-13-aza-15-hydroxy-16-(3-chlorophenoxy)-17,18,19,20-tetranor-11a-carbathrombanoic acid, (5Z,15ξ)-9,11-methano-13-aza-15-hydroxy-16-(3-chlorophenoxy)-17,18,19,20-tetranor-11a-carbathromb-5-enoic acid, (15ξ)-9,11-methano-13-aza-15-hydroxy-16-(3-chlorophenoxy)-17,18,19,20-tetranor-11a-carbathrombanoic acid, (5Z,15ξ)-9,11-methano-10,10-dimethyl-13-aza-15-hydroxy-16-(3-trifluoromethylphenoxy)-17,18,19,20-tetranor-11a-carbathromb-5-enoic acid, (15ξ)-9,11-methano-10,10-dimethyl-13-aza-15-hydroxy-16-(3-trifluoromethylphenoxy)-17,18,19,20-tetranor-11a-carbathrombanoic acid, (5Z,15ξ)-9,11-methano-13-aza-15-hydroxy-16-(3-trifluoromethylphenoxy)-17,18,19,20-tetranor-11a-carbathromb-5-enoic acid, (15ξ)-9,11-methano-13-aza-15-hydroxy-16-(3-trifluoromethylphenoxy)-17,18,19,20-tetranor-11a-carbathrombanoic acid, (5Z,15ξ)-9,11-methano-10,10-dimethyl-13-aza-15-hydroxy-16-(3-fluorophenoxy)-17,18,19,20-tetranor-11a-carbathromb-5-enoic acid, (15ξ)-9,11-methano-10,10-dimethyl-13-aza-15-hydroxy-16-(3-fluorophenoxy)-17,18,19,20-tetranor-11a-carbathrombanoic acid, (5Z,15ξ)-9,11-methano-13-aza-15-hydroxy-16-(3-fluorophenoxy)-17,18,19,20-tetranor-11a-carbathromb-5-enoic acid, (15ξ)-9,11-methano-13-aza-15-hydroxy-16-(3-fluorophenoxy)-17,18,19,20-tetranor-11a-carbathrombanoic acid, (5Z,15ξ)-9,11-methano-10,10-dimethyl-13-aza-15-hydroxy-16-(3-hydroxyphenoxy)-17,18,19,20-tetranor-11a-carbathromb-5-enoic acid, (15ξ)-9,11-methano-10,10-dimethyl-13-aza-15-hydroxy-16-(3-hydroxyphenoxy)-17,18,19,20-tetranor-11a-carbathrombanoic acid, (5Z,15ξ)-9,11-methanol-13-aza-15-hydroxy-16-(3-hydroxyphenoxy)-17,18,19,20-tetranor-11a-carbathromb-5-enoic acid, (15ξ)-9,11-methano-13-aza-15-hydroxy-16-(3-hydroxyphenoxy)-17,18,19,20-tetranor-11a-carbathrombanoic acid, (5Z,15ξ)-9,11-methano-10,10-dimethyl-13-aza-15-hydroxy-16-(3-aminophenoxy)-17,18,19,20-tetranor-11a-carbathromb-5-enoic acid, (15ξ)-9,11-methano-10,10-dimethyl-13-aza-15-hydroxy-16-(3-aminophenoxy)-17,18,19,20-tetranor-11a-carbathrombanoic acid, (5Z,15ξ)-9,11-methano-13-aza-15-hydroxy-16-(3-aminophenoxy)-17,18,19,20-tetranor-11a-carbathromb-5-enoic acid, (15ξ)-9,11-methano-13-aza-15-hydroxy-16-(3-aminophenoxy)-17,18,19,20-tetranor-11a-carbathrombanoic acid, (5Z,15ξ)-9,11-methano-10,10-dimethyl-13-aza-15-hydroxy-16-phenylthio-17,18,19,20-tetranor-11a-carbathromb-5-enoic acid, (15ξ)-9,11-methano-10,10-dimethyl-13-aza-15-hydroxy-16-phenylthio-17,18,19,20-tetranor-11a-carbathrombanoic acid, (5Z,15ξ)-9,11-methano-13-aza-15-hydroxy-16-phenylthio-17,18,19,20-tetranor-11a-carbathromb-5-enoic acid, (15ξ)-9,11-methano-13-aza-15-hydroxy-16-phenylthio-17,18,19,20-tetranor-11a-carbathrombanoic acid, (5Z,15ξ)-9,11-methano-10,10-dimethyl-13-aza-15-hydroxy-16-(3-methylphenylthio)-17,18,19,20-tetranor-11a-carbathromb-5-enoic acid, (15ξ)-9,11-methano-10,10-dimethyl-13-aza-15-hydroxy-16-(3-methylphenylthio)-17,18,19,20-tetranor-11a-carbathrombanoic acid, (5Z,15ξ)-9,11-methano-13-aza-15-hydroxy-16-(3-methylphenylthio)-17,18,19,20-tetranor-11a-carbathromb-5-enoic acid, (5ξ)-9,11-methano-13-aza-15-hydroxy-16-(3-methylphenylthio)-17,18,19,20-tetranor-11a-carbathrombanoic acid, (5Z,15ξ)-9,11-methano-10,10-dimethyl-13-aza-15-hydroxy-16-(3-ethylphenylthio)-17,18,19,20-tetranor-11a-carbathromb-5-enoic acid, (15ξ)-9,11-methano-10,10-dimethyl-13-aza-15-hydroxy-16-(3-ethylphenylthio)-17,18,19,20-tetranor-11a-carbathrombanoic acid, (5Z,15ξ)-9,11-methano-13-aza-15-hydroxy-16-(3-ethylphenylthio)-17,18,19,20-tetranor-11a-carbathromb-5-enoic acid, (15ξ)-9,11-methano-13-aza-15-hydroxy-16-(3-ethylphenylthio)-17,18,19,20-tetranor-11a-carbathrombanoic acid, (5Z,15ξ)-9,11-methano-10,10-dimethyl-13-aza-15-hydroxy-16-(3-propylphenylthio)-17,18,19,20-tetranor-11a-carbathromb-5-enoic acid, (15ξ)-9,11-methano-10,10-dimethyl-13-aza-15-hydroxy-16-(3-propylphenylthio)-17,18,19,20-tetranor-11a-carbathrombanoic acid, (5Z,15ξ)-9,11-methano-13-aza-15-hydroxy-16-(3-propylphenylthio)-17,18,19,20-tetranor-11a-carbathromb-5-enoic acid, (15ξ)-9,11-methano-13-aza-15-hydroxy-16-(3-propylphenylthio)-17,18,19,20-tetranor-11a-carbathrombanoic acid, (5Z,15ξ)-9,11-methano-10,10-dimethyl-13-aza-15-hydroxy-16-(3-tert-butylphenylthio)-17,18,19,20-tetranor-11a-carbathromb-5-enoic acid, (15ξ)-9,11-methano-10,10-dimethyl-13-aza-15-hydroxy-16-(3-tert-butylphenylthio)-17,18,19,20-tetranor-11a-carbathrombanoic acid, (5Z,15ξ)-9,11-methano-13-aza-15-hydroxy-16-(3-tert-butylphenylthio)-17,18,19,20-tetranor-11a-carbathromb-5-enoic acid, (15ξ)-9,11-methano-13-aza-15-hydroxy-16-(3-tert-butylphenylthio)-17,18,19,20-tetranor-11a-carbathrombanoic acid, (5Z,15ξ)-9,11-methano-10,10-dimethyl-13-aza-15-hydroxy-16-(3-chlorophenylthio)-17,18,19,20-tetranor-11a-carbathromb-5-enoic acid, (15ξ)-9,11-methano-10,10-dimethyl-13-aza-15-hydroxy-16-(3-chlorophenylthio)-17,18,19,20-tetranor-11a-carbathrombanoic acid, (5Z,15ξ)-9,11-methano-13-aza-15-hydroxy-16-(3-chlorophenylthio)-17,18,19,20-tetranor-11a-carbathromb-5-enoic acid, (15ξ)-9,11-methano-13-aza-15-hydroxy-16-(3-chlorophenylthio)-17,18,19,20-tetranor-11a-carbathrombanoic acid, (5Z,15ξ)-9,11-methano-10,10-dimethyl-13-aza-15-hydroxy-16-(3-fluorophenylthio)-17,18,19,20-tetranor-11a-carbathromb-5-enoic acid, (15ξ)-9,11-methano-10,10-dimethyl-13-aza-15-hydroxy-16-(3-fluorophenylthio)-17,18,19,20-tetranor-11a-carbathrombanoic acid, (5Z,15ξ)-9,11-methano-13-aza-15-hydroxy-16-(3-fluorophenylthio)-17,18,19,20-tetranor-11a-carbathromb-5-enoic acid, (15ξ)-9,11-methano-13-aza-15-hydroxy-15-(3-fluorophenylthio)-17,18,19,20-tetranor-11a-carbathrombanoic acid, (5Z,15ξ)-9,11-methano-10,10-dimethyl-13-aza-15-hydroxy-16-(3-trifluoromethylphenylthio)-17,18,19,20-tetranor-11a-carbathromb-5-enoic acid, (15ξ)-9,11-methano-10,10-dimethyl-13-aza-15-hydroxy-16-(3-trifluoromethylphenylthio)-17,18,19,20-tetranor-11a-carbathrombanoic acid, (5Z,15ξ)-9,11-methano-13-aza-15-hydroxy-16-(3-trifluoromethylphenylthio)-17,18,19,20-tetranor-11a-carbathromb-5-enoic acid, (15ξ)-9,11-methano-13-aza-15-hydroxy-16-(3-trifluoromethylphenylthio)-17,18,19,20-tetranor-11a-carbathrombanoic acid, (5Z,15ξ)-9,11-methano-10,10-dimethyl-13-aza-15-hydroxy-16-(3-hydroxyphenylthio)-17,18,19,20-tetranor-11a-carbathromb-5-enoic acid, (15ξ)-9,11-methano-10,10-dimethyl-13-aza-15-hydroxy-16-(3-hydroxyphenylthio)-17,18,19,20-tetranor-11a-carbathrombanoic acid, (5Z,15ξ)-9,11-methano-13-aza-15-hydroxy-16-(3-hydroxyphenylthio)-17,18,19,20-tetranor-11a-carbathromb-5-enoic acid, (15ξ)-9,11-methano-13-aza-15-hydroxy-16-(3-hydroxyphenylthio)-17,18,19,20-tetranor-11a-carbathrombanoic acid, (5Z,15ξ)-9,11-methano-10,10-dimethyl-13-aza-15-hydroxy-16-(3-aminophenylthio)-17,18,19,20-tetranor-11a-carbathromb-5-enoic acid, (15ξ)-9,11-methano-10,10-dimethyl-13-aza-15-hydroxy-16-(3-aminophenylthio)-17,18,19,20-tetranor-11a-carbathrombanoic acid, (5Z,15ξ)-9,11-methano-13-aza-15-hydroxy-16-(3-aminophenylthio)-17,18,19,20-tetranor-11a-carbathromb-5-enoic acid, (15ξ)-9,11-methano-13-aza-15-hydroxy-16-(3-aminophenylthio)-17,18,19,20-tetranor-11a-carbathrombanoic acid, (5Z,15ξ)-9,11-methano-10,10-dimethyl-13-aza-15-hydroxy-16-(4-methylphenoxy)-17,18,19,20-tetranor-11a-carbathromb-5-enoic acid, (15ξ)-9,11-methano-10,10-dimethyl-13-aza-15-hydroxy-16-(4-methylphenoxy)-17,18,19,20-tetranor-11a-carbathrombanoic acid, (5Z,15ξ)-9,11-methano-13-aza-15-hydroxy-16-(4-methylphenoxy)-17,18,19,20-tetranor-11a-carbathromb-5-enoic acid, (15ξ)-9,11-methano-13-aza-15-hydroxy-16-(4-methylphenoxy)-17,18,19,20-tetranor-11a-carbathrombanoic acid, (5Z,15ξ)-9,11-methano-10,10-dimethyl-13-aza-15-hydroxy-16-(4-ethylphenoxy)-17,18,19,20-tetranor-11a-carbathromb-5-enoic acid, (15ξ)-9,11-methano-10,10-dimethyl-13-aza-15-hydroxy-16-(4-ethylphenoxy)-17,18,19,20-tetranor-11a-carbathrombanoic acid, (5Z,15ξ)-9,11-methano-13-aza-15-hydroxy-16-(4-ethylphenoxy)-17,18,19,20-tetranor-11a-carbathromb-5-enoic acid, (15ξ)-9,11-methano-13-aza-15-hydroxy-16-(4-ethylphenoxy)-17,18,19,20-tetranor-11a-carbathrombanoic acid, (5Z,15ξ)-9,11-methano-10,10-dimethyl-13-aza-15-hydroxy-16-(4-propylphenoxy)-17,18,19,20-tetranor-11a-carbathromb-5-enoic acid, (15ξ)-9,11-methano-10,10-dimethyl-13-aza-15-hydroxy-16-(4-propylphenoxy)-17,18,19,20-tetranor-11a-carbathrombanoic acid, (5Z,15ξ)-9,11-methano-13-aza-15-hydroxy-16-(4-propylphenoxy)-17,18,19,20-tetranor-11a-carbathromb-5-enoic acid, (15ξ)-9,11-methano-13-aza-15-hydroxy-16-(4-propylphenoxy)-17,18,19,20-tetranor-11a-carbathrombanoic acid, (5Z,15ξ)-9,11-methano-10,10-dimethyl-13-aza-15-hydroxy-16-(4-tert-butylphenoxy)-17,18,19,20-tetranor-11a-carbathromb-5-enoic acid, (15ξ)-9,11-methano-10,10-dimethyl-13-aza-15-hydroxy-16-(4-tert-butylphenoxy)-17,18,19,20-tetranor-11a-carbathrombanoic acid, (5Z,15ξ)-9,11-methano-13-aza-15-hydroxy-16-(4-tert-butylphenoxy)-17,18,19,20-tetranor-11a-carbathromb-5-enoic acid, (15ξ)-9,11-methano-13-aza-15-hydroxy-16-(4-tert-butylphenoxy)-17,18,19,20-tetranor-11a-carbathrombanoic acid, (5Z,15ξ)-9,11-methano-10,10-dimethyl-13-aza-15-hydroxy-16-(4-chlorophenoxy)-17,18,19,20-tetranor-11a-carbathromb-5-enoic acid, (15ξ)-9,11-methano-10,10-dimethyl-13-aza-15-hydroxy-16-(4-chlorophenoxy)-17,18,19,20-tetranor-11a-carbathrombanoic acid, (5Z,15ξ)-9,11-methano-13-aza-15-hydroxy-16-(4-chlorophenoxy)-17,18,19,20-tetranor-11a-carbathromb-5-enoic acid, (15ξ)-9,11-methano-13-aza-15-hydroxy-16-(4-chlorophenoxy)-17,18,19,20-tetranor-11a-carbathrombanoic acid, (5Z,15ξ)-9,11-methano-10,10-dimethyl-13-aza-15-hydroxy-16-(4-fluorophenoxy)-17,18,19,20-tetranor-11a-carbathromb-5-enoic acid, (15ξ)-9,11-methano-10,10-dimethyl-13-aza-15-hydroxy-16-(4-fluorophenoxy)-17,18,19,20-tetranor-11a-carbathrombanoic acid, (5Z,15ξ)-9,11-methano-13-aza-15-hydroxy-16-(4-fluorophenoxy)-17,18,19,20-tetranor-11a-carbathromb-5-enoic acid, (15ξ)-9,11-methano-13-aza-15-hydroxy-16-(4-fluorophenoxy)-17,18,19,20-tetranor-11a-carbathrombanoic acid, (5Z,15ξ)-9,11-methano-10,10-dimethyl-13-aza-15-hydroxy-16-(4-trifluoromethylphenoxy)-17,18,19,20-tetranor-11a-carbathromb-5-enoic acid, (15ξ)-9,11-methano-10,10-dimethyl-13-aza-15-hydroxy-16-(4-trifluoromethylphenoxy)-17,18,19,20-tetranor-11a-carbathrombanoic acid, (5Z,15ξ)-9,11-methano-13-aza-15-hydroxy-16-(4-trifluoromethylphenoxy)-17,18,19,20-tetranor-11a-carbathromb-5-enoic acid, (15ξ)-9,11-methano-13-aza-15-hydroxy-16-(4-trifluoromethylphenoxy)-17,18,19,20-tetranor-11a-carbathrombanoic acid, (5Z,15ξ)-9,11-methano-10,10-dimethyl-13-aza-15-hydroxy-16-(4-hydroxyphenoxy)-17,18,19,20-tetranor-11a-carbathromb-5-enoic acid, (15ξ)-9,11-methano-10,10-dimethyl-13-aza-15-hydroxy-16-(4-hydroxyphenoxy)-17,18,19,20-tetranor-11a-carbathrombanoic acid, (5Z,15ξ)-9,11-methano-13-aza-15-hydroxy-16-(4-hydroxyphenoxy)-17,18,19,20-tetranor-11a-carbathromb-5-enoic acid, (15ξ)-9,11-methano-13-aza-15-hydroxy-16-(4-hydroxyphenoxy)-17,18,19,20-tetranor-11a-carbathrombanoic acid, (5Z,15ξ)-9,11-methano-10,10-dimethyl-13-aza-15-hydroxy-16-(4-aminophenoxy)-17,18,19,20-tetranor-11a-carbathromb-5-enoic acid, (15ξ)-9,11-methano-10,10-dimethyl-13-aza-15-hydroxy-16-(4-aminophenoxy)-17,18,19,20-tetranor-11a-carbathrombanoic acid, (5Z,15ξ)-9,11-methano-13-aza-15-hydroxy-16-(4-aminophenoxy)-17,18,19,20-tetranor-11a-carbathromb-5-enoic acid, (15ξ)-9,11-methano-13-aza-15-hydroxy-16-(4-aminophenoxy)-17,18,19,20-tetranor-11a-carbathrombanoic acid, (5Z,15ξ)-9,11-methano-10,10-dimethyl-13-aza-15-hydroxy-16-(4-methylphenylthio)-17,18,19,20-tetranor-11a-carbathromb-5-enoic acid, (15ξ)-9,11-methano-10,10-dimethyl-13-aza-15-hydroxy-16-(4-methylphenylthio)-17,18,19,20-tetranor-11a-carbathrombanoic acid, (5Z,15ξ)-9,11-methano-13-aza-15-hydroxy-16-(4-methylphenylthio)-17,18,19,20-tetranor-11a-carbathromb-5-enoic acid, (15ξ)-9,11-methano-13-aza-15-hydroxy-16-(4-methylphenylthio)-17,18,19,20-tetranor-11a-carbathrombanoic acid, (5Z,15ξ)-9,11-methano-10,10-dimethyl-13-aza-15-hydroxy-16-(4-ethylphenylthio)-17,18,19,20-tetranor-11a-carbathromb-5-enoic acid, (15ξ)-9,11-methano-10,10-dimethyl-13-aza-15-hydroxy-16-(4-ethylphenylthio)-17,18,19,20-tetranor-11a-carbathrombanoic acid, (5Z,15ξ)-9,11-methano-13-aza-15-hydroxy-16-(4-ethylphenylthio)-17,18,19,20-tetranor-11a-carbathromb-5-enoic acid, (15ξ)-9,11-methano-13-aza-15-hydroxy-16-(4-ethylphenylthio)-17,18,19,20-tetranor-11a-carbathrombanoic acid, (5Z,15ξ)-9,11-methano-10,10-dimethyl-13-aza-15-hydroxy-16-(4-propylphenylthio)-17,18,19,20-tetranor-11a-carbathromb-5-enoic acid, (15ξ)-9,11-methano-10,10-dimethyl-13-aza-15-hydroxy-16-(4-propylphenylthio)-17,18,19,20-tetranor-11a-carbathrombanoic acid, (5Z,15ξ)-9,11-methano-13-aza-15-hydroxy-16-(4-propylphenylthio)-17,18,19,20-tetranor-11a-carbathromb-5-enoic acid, (15ξ)-9,11-methano-13-aza-15-hydroxy-16-(4-propylphenylthio)-17,18,19,20-tetranor-11a-carbathrombanoic acid, (5Z,15ξ)-9,11-methano-10,10-dimethyl-13-aza-15-hydroxy-16-(4-tert-butylphenylthio)-17,18,19,20-tetranor-11a-carbathromb-5-enoic acid, (15ξ)-9,11-methano-10,10-dimethyl-13-aza-15-hydroxy-16-(4-tert-butylphenylthio)-17,18,19,20-tetranor-11a-carbathrombanoic acid, (5Z,15ξ)-9,11-methano-13-aza-15-hydroxy-16-(4-tert-butylphenylthio)-17,18,19,20-tetranor-11a-carbathromb-5-enoic acid, (15ξ)-9,11-methano-13-aza-15-hydroxy-16-(4-tert-butylphenylthio)-17,18,19,20-tetranor-11a-carbathrombanoic acid, (5Z,15ξ)-9,11-methano-10,10-dimethyl-13-aza-15-hydroxy-16-(4-chlorophenylthio)-17,18,19,20-tetranor-11a-carbathromb-5-enoic acid, (15ξ)-9,11-methano-10,10-dimethyl-13-aza-15-hydroxy-16-(4-chlorophenylthio)-17,18,19,20-tetranor-11a-carbathrombanoic acid, (5Z,15ξ)-9,11-methano-13-aza-15-hydroxy-16-(4-chlorophenylthio)-17,18,19,20-tetranor-11a-carbathromb-5-enoic acid, (15ξ)-9,11-methano-13-aza-15-hydroxy-16-(4-chlorophenylthio)-17,18,19,20-tetranor-11a-carbathrombanoic acid, (5Z,15ξ)-9,11-methano-10,10-dimethyl-13-aza-15-hydroxy-16-(4-fluorophenylthio)-17,18,19,20-tetranor-11a-carbathromb-5-enoic acid, (15ξ)-9,11-methano-10,10-dimethyl-13-aza-15-hydroxy-16-(4-fluorophenylthio)-17,18,19,20-tetranor-11a-carbathrombanoic acid, (5Z,15ξ)-9,11-methano-13-aza-15-hydroxy-16-(4-fluorophenylthio)-17,18,19,20-tetranor-11a-carbathromb-5-enoic acid, (15ξ)-9,11-methano-13-aza-15-hydroxy-16-(4-fluorophenylthio)-17,18,19,20-tetranor-11a-carbathrombanoic acid, (5Z,15ξ)-9,11-methano-10,10-dimethyl-13-aza-15-hydroxy-16-(4-trifluoromethylphenylthio)-17,18,19,20-tetranor-11a-carbathromb-5-enoic acid, (15ξ)-9,11-methano-10,10-dimethyl-13-aza-15-hydroxy-16-(4-trifluoromethylphenylthio)-17,18,19,20-tetranor-11a-carbathrombanoic acid, (5Z,15ξ)-9,11-methano-13-aza-15-hydroxy-16-(4-trifluoromethylphenylthio)-17,18,19,20-tetranor-11a-carbathromb-5-enoic acid, (15ξ)-9,11-methano-13-aza-15-hydroxy-16-(4-trifluoromethylphenylthio)-17,18,19,20-tetranor-11a-carbathrombanoic acid, (5Z,15ξ)-9,11-methano-10,10-dimethyl-13-aza-15-hydroxy-16-(4-hydroxyphenylthio)-17,18,19,20-tetranor-11a-carbathromb-5-enoic acid, (15ξ)-9,11-methano-10,10-dimethyl-13-aza-15-hydroxy-16-(4-hydroxyphenylthio)-17,18,19,20-tetranor-11a-carbathrombanoic acid; (5Z,15ξ)-9,11-methano-13-aza-15-hydroxy-16-(4-hydroxyphenylthio)-17,18,19,20-tetranor-11a-carbathromb-5-enoic acid, (15ξ)-9,11-methano-13-aza-15-hydroxy-16-(4-hydroxyphenylthio)-17,18,19,20-tetranor-11a-carbathrombanoic acid, (5Z,15ξ)-9,11-methano-10,10-dimethyl-13-aza-15-hydroxy-16-(4-aminophenylthio)-17,18,19,20-tetranor-11a-carbathromb-5-enoic acid, (15ξ)-9,11-methano-10,10-dimethyl-13-aza-15-hydroxy-16-(4-aminophenylthio)-17,18,19,20-tetranor-11a-carbathrombanoic acid, (5Z,15ξ)-9,11-methano-13-aza-15-hydroxy-16-(4-aminophenylthio)-17,18,19,20-tetranor-11a-carbathromb-5-enoic acid, (15ξ)-9,11-methano-13-aza-15-hydroxy-16-(4-aminophenylthio)-17,18,19,20-tetranor-11a-carbathrombanoic acid, (5Z,15ξ)-9,11-methano-10,10-dimethyl-13-aza-15-hydroxy-17-phenyl-18,19,20-trinor-11a-carbathromb-5- enoic acid, (15ξ)-9,11-methano-10,10-dimethyl-13-aza-15-hydroxy-17-phenyl-18,19,20-trinor-11a-carbathrombanoic acid, (5Z,15ξ)-9,11-methano-13-aza-15-hydroxy-17-phenyl-18,19,20-trinor-11a-carbathromb-5-enoic acid, (15ξ)-9,11-methano-13-aza-15-hydroxy-17-phenyl-18,19,20-trinor-11a-carbathrombanoic acid, (5Z,15ξ)-9,11-methano-10,10-dimethyl-13-aza-15-hydroxy-17-oxa-20-ethyl-11a-carbathromb-5-enoic acid, (15ξ)-9,11-methano-10,10-dimethyl-13-aza-15-hydroxy-17-oxa-20-ethyl-11a-carbathrombanoic acid, (5Z,15ξ)-9,11-methano-13-aza-15-hydroxy-17-oxa-20-ethyl-11a-carbathromb-5-enoic acid, (15ξ)-9,11-methano-13-aza-15-hydroxy-17-oxa-20-ethyl-11a-carbathrombanoic acid, (5Z,15ξ)-9,11-methano-10,10-dimethyl-13-aza-15-hydroxy-17-thia-20-ethyl-11a-carbathromb-5-enoic acid, (15ξ)-9,11-methano-10,10-dimethyl-13-aza-15-hydroxy-17-thia-20-ethyl-11a-carbathrombanoic acid, (5Z,15ξ)-9,11-methano-13-aza-15-hydroxy-17-thia-20-ethyl-11a-carbathromb-5-enoic acid, (15ξ)-9,11-methano-13-aza-15-hydroxy-17-thia-20-ethyl-11a-carbathrombanoic acid, and the corresponding 15-deoxy analogues, the corresponding 5-oxa analogues, and the corresponding 1,5-inter-p-phenylene-2,3,4-trinor analogues, i.e. compounds of the general formula V wherein A represents the group

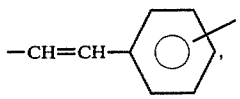

and their alkyl esters, and cyclodextrin clathrates thereof, and non-toxic salts thereof.

Particularly preferred 11a-carbathrombanoic acid analogues of the invention are (5Z,15ξ)-9,11-methano-10,10-dimethyl-13-aza-15-hydroxy-11a-carbathromb-5-enoic acid, (5Z,15ξ)-9,11-methano-10,10-dimethyl-13-aza-15-hydroxy-20-methyl-11a-carbathromb-5-enoic acid, (5Z,15ξ)-9,11-methano-10,10-dimethyl-13-aza-15-hydroxy-20-ethyl-11a-carbathromb-5-enoic acid, (5Z,15ξ)-9,11-methano-10,10-dimethyl-13-aza-15-hydroxy-20-propyl-11a-carbathromb-5-enoic acid, (5Z,15ξ)-9,11-methano-10,10-dimethyl-13-aza-15-hydroxy-17-methyl-20-ethyl-11a-carbathromb-5-enoic acid, (5Z,15ξ)-9,11-methano-10,10-dimethyl-13-aza-15-hydroxy-17-thia-20-ethyl-11a-carbathromb-5-enoic acid, (5Z,15ξ)-9,11-methano-10,10-dimethyl-13-aza-15-hydroxy-16-phenyl-17,18,19,20-tetranor-11a-carbathromb-5-enoic acid, (5Z,15ξ)-9,11-methano-10,10-dimethyl-13-aza-15-hydroxy-16-phenoxy-17,18,19,20-tetranor-11a-carbathromb-5-enoic acid, (5Z,15ξ)-9,11-methane-10,10-dimethyl-13-aza-15-hydroxy-16-(4-methylphenoxy)-17,18,19,20-tetranor-11a-carbathromb-5-enoic acid, (5Z,15ξ)-9,11-methano-10,10-dimethyl-13-aza-15-hydroxy-16-(4-ethylphenoxy)-17,18,19,20-tetranor-11a-carbathromb-5-enoic acid, (5Z,15ξ)-9,11-methano-10,10-dimethyl-13-aza-15-hydroxy-16-(4-propylphenoxy)-17,18,19,20-tetranor-11a-carbathromb-5-enoic acid, (5Z,15ξ)-9,11-methano-10,10-dimethyl-13-aza-15-hydroxy-16-(4-chlorophenoxy)-17,18,19,20-tetranor-11a-carbathromb-5-enoic acid, (5Z,15ξ)-9,11-methano-10,10-dimethyl-13-aza-15-hydroxy-16-(3-chlorophenoxy)-17,18,19,20-tetranor-11a-carbathromb-5-enoic acid, (5Z,15ξ)-9,11-methano-10,10-dimethyl-13-aza-15-hydroxy-16-(3-trifluoromethylphenoxy)-17,18,19,20-tetranor-11a-carbathromb-5-enoic acid, (5Z,15ξ)-9,11-methano-10,10-dimethyl-13-aza-15-hydroxy-16-phenylthio-17,18,19,20-tetranor-11a-carbathromb-5-enoic acid, (5Z,15ξ)-9,11-methano-10,10-dimethyl-13-aza-15-hydroxy-16-(4-methylphenylthio)-17,18,19,20-tetranor-11a-carbathromb-5-enoic acid, (5Z,15ξ)-9,11-methano-10,10-dimethyl-13-aza-15-hydroxy-16-(4-ethylphenylthio)-17,18,19,20-tetranor-11a-carbathromb-5-enoic acid, (5Z,15ξ)-9,11-methano-10,10-dimethyl-13-aza-15-hydroxy-16-(4-propylphenylthio)-17,18,19,20-tetranor-11a-carbathromb-5-enoic acid, (5Z,15ξ)-9,11-methano-10,10-dimethyl-13-aza-15-hydroxy-16-(4-chlorophenylthio)-17,18,19,20-tetranor-11a-carbathromb-5-enoic acid, (5Z,15ξ)-9,11-methano-10,10-dimethyl-13-aza-15-hydroxy-16-(3-chlorophenylthio)-17,18,19,20-tetranor-11a-carbathromb-5-enoic acid, (5Z,15ξ)-9,11-methano-10,10-dimethyl-13-aza-15-hydroxy-16-(3-trifluorophenylthio)-17,18,19,20-tetranor-11a-carbathromb-5-enoic acid, (15ξ)-9,11-methano-10,10-dimethyl-13-aza-15-hydroxy-16-phenylthio-17,18,19,20-tetranor-11a-carbathrombanoic acid, (5Z)-9,11-methano-10,10-dimethyl-13-aza-11a-carbathromb-5-enoic acid, (5Z)-9,11-methano-10,10-dimethyl-13-aza-16-phenylthio-17,18,19,20-tetranor-11a-carbathromb-5-enoic acid, (5Z)-9,11-methano-13-aza-11a-carbathromb-5-enoic acid, (15ξ)-5-oxa-9,11-methano-10,10-dimethyl-13-aza-15-hydroxy-16-(4-ethylphenylthio)-17,18,19,20-tetranor-11a-carbathrombanoic acid, (5EZ,15ξ)-1,5-inter-p-phenylene-9,11-methano-10,10-dimethyl-13-aza-15-hydroxy-16-(4-ethylphenylthio)-2,3,4,17,18,19,20-heptanor-11a-carbathromb-5-enoic acid, and their methyl ester, and cyclodextrin clathrates thereof, and non-toxic acids thereof.

The following reference examples and examples illustrate the preparation of the compounds of the present invention. In the reference examples and examples, "TLC", "IR", "NMR" and "MS" represent thin layer chromatography, infrared absorption spectrum, nuclear magnetic resonance spectrum and mass spectrum, respectively. The proportion of the solvents described in the part of separation by chromatography indicates a volume ratio, and the solvent in the parentheses indicates the developing solvent used. Unless otherwise indicates, the infrared absorption spectrum was determined in a liquid film method, and the nuclear magnetic resonance spectrum was determined in deuterochloroform (CDCl$_3$) solution.

Reference Example 1

2-Methylenenorpinane 1.143 g of sodium hydride (content: 63%) suspended in 15 ml of dimethyl sulfoxide was stirred at 70° C. for 1 hour under a nitrogen atmosphere, and a solution of 10.71 g of methyltriphenylphosphonium bromide in 30 ml of dimethyl sulfoxide was added thereto dropwise under ice-cooling, followed by stirring at room temperature for 15 minutes. To the resulting solution was added dropwise a solution of 2.169 g of 2-oxonorpinane [described in Chem. Ber., 100, 3627 (1967)] in 6 ml of dimethyl sulfoxide, followed by stirring at room temperature for 1 hour. The reaction mixture was poured into ice-water and extracted with pentane. The extract was dried over anhydrous magnesium sulfate, and the solvent was distilled off to obtain 900 mg of the titled compound.

NMR: δ=4.5 (2H, m).

Reference Example 2

2-(2-Hydroxy)ethyl-2-norpinene 900 mg of 2-methylenenorpinane (prepared in Reference Example 1) and 200 mg of paraformaldehyde were placed in a sealed tube and reacted at 180° C. for 18 hours. The reaction mixture was purified by silica gel column chromatography using a mixture of cyclohexane and ethyl acetate (10:1) as an eluent to obtain 622 mg of the title compound.

TLC (cyclohexane:ethyl acetate): Rf=0.38.
NMR: $\delta$=5.4–5.2 (1H, m), 3.63 (2H, t).

In the same manner, the following compound was obtained from β-pinene.

(a) 2-(2-Hydroxy)ethyl-6,6-dimethyl-2-norpinene
Boiling Point: 133° C./30 mmHg.
NMR: $\delta$=5.6–5.1 (2H, m), 3.53 (2H, t), 1.27 (3H, s), 0.85 (3H, s).

Reference Example 3

2-[2-(Tetrahydropyran-2-yloxy)ethyl]-2-norpinene

A mixture of 600 mg of the norpinene compound (prepared in Reference Example 2), 0.5 ml of 2,3-dihydropyran, a catalytic amount of p-toluenesulfonic acid and 10 ml of methylene chloride was stirred at room temperature for 30 minutes. 0.2 ml of triethylamine was added to the reaction mixture, followed by concentration under reduced pressure. The residue was purified by silica gel column chromatography using a mixture of cyclohexane and ethyl acetate (49:1) as an eluent to obtain 812 mg of the titled compound.

TLC (cyclohexane:ethyl acetate=20:1): Rf=0.25.
NMR: $\delta$=5.30–5.15 (1H, m), 4.65–4.50 (1H, m).

In the same manner, the following compound was obtained from the compound of Reference Example 2(a).

(a) 2-[2-(Tetrahydropyran-2-yloxy)ethyl]-6,6-dimethyl-2-norpinene

TLC (cyclohexane:ethyl acetate=20:1): Rf=0.42.

Reference Example 4

2-[3-Oxa-7-(tetrahydropyran-2-yloxy)heptyl]-6,6-dimethyl-2-norpinene 20 g of sodium hydride (content: 64.1%) suspended in 150 ml of dimethylsulfoxide was stirred at 60° C. for 30 minutes under a nitrogen atmosphere, and a solution of 9.27 g of 2-(2-hydroxy)ethyl-6,6-dimethyl-2-norpinene [prepared in Reference Example 2(a)] in 10 ml of dimethyl sulfoxide was added thereto under ice-cooling, followed by stirring for 30 minutes. To the resulting solution was added a solution of 10.7 g of 1-chloro-4-(tetrahydropyran-2-yloxy)butane in 10 ml of dimethyl sulfoxide, followed by stirring overnight at 40° C., and then for 2 hours at 60° C. The reaction mixture was poured into ice-water and extracted with ethyl acetate. The extract was washed with successively water and a saturated sodium chloride aqueous solution, dried over anhydrous magnesium sulfate and concentrated under reduced pressure. The residue was distilled to obtain 12 g of the title compound.

Boiling Point: 140°–155° C./1 mmHg.
MNR: $\delta$=5.30–5.07 (1H, m), 4.63–4.40 (1H, m), 4.07–3.13 (8H, m), 1.30 (3H, s), 0.83 (3H, s).
IR: $\nu$=2930, 1440, 1360, 1200, 1120, 1030 cm$^{-1}$.
MS: m/e=322(M+), 238, 195, 105, 85.

Reference Example 5

(2α)-2-[2-(Tetrahydropyran-2-yloxy)ethyl]-3-hydroxynorpinane 10 ml of a 1 M tetrahydrofuran solution of diborane was added dropwise to a solution of 800 mg of the norpinene compound (prepared in Reference Example 3) in 5 ml of tetrahydrofuran at 0° C. under a nitrogen atmosphere, followed by stirring at room temperature for 1 hour. To the reaction mixture were added 0.75 ml of water and 2.5 ml of a 3 N sodium hydroxide aqueous solution, and further was added dropwise a large excess of 30% aqueous hydrogen peroxide, followed by stirring at 50° C. for 1 hour. The reaction mixture was extracted with diethyl ether, and the extract was washed with a saturated sodium chloride aqueous solution, dried over anhydrous magnesium sulfate and concentrated under reduced pressure. The residue was purified by silica gel column chromatography using a mixture of cyclohexane and ethyl acetate (2:1) as an eluent to obtain 854 mg of the title compound.

TLC (cyclohexane:ethyl acetate=2:1): Rf=0.32.
NMR: $\delta$=4.65–4.50 (1H, m).

In the same manner, the following compounds were obtained from the compounds of Reference Example 3(a) and Reference Example 4.

(a) (2α)-2-[2-(Tetrahydropyran-2-yloxy)ethyl]-3-hydroxy-6,6-dimethylnorpinane

TLC (cyclohexane:ethyl acetate=2:1): Rf=0.31.
NMR: $\delta$=4.4 (1H, m), 1.2 (3H, s), 0.9 (3H, s).

(b) (2α)-2-[3-Oxa-7-(tetrahydropyran-2-yloxy)heptyl]-3-hydroxy-6,6-dimethylnorpinane TLC (cyclohexane:ethyl acetate=7:3): Rf=0.56.
NMR: $\delta$=4.60–4.37 (1H, m), 4.27–3.03 (9H, m), 1.17 (3H, s), 0.88 (3H, s).
MS: m/e=340(M+), 322, 279, 255, 239, 187, 169, 85.

Reference Example 6

(2α)-2-[2-(Tetrahydropyran-2-yloxy)ethyl]norpinan-3-one

A mixture of 834 mg of the hydroxy compound (prepared in Reference Example 5), 10 ml of diethyl ether and 10 ml of a chromic acid solution (prepared from 1.9 g of chromium trioxide, 6.4 g of manganese sulfate, 2.1 ml of concentrated sulfuric acid and 47.5 ml of water) was stirred at 0° C. for 1 hour. The reaction mixture was diluted with diethyl ether, washed successively with water, a saturated sodium bicarbonate aqueous solution and a saturated sodium chloride aqueous solution, dried over anhydrous magnesium sulfate and concentrated under reduced pressure. The residue was purified by silica gel column chromatography using a mixture of cyclohexane and ethyl acetate (10:1) as an eluent to obtain 562 mg of the title compound.

TLC (cyclohexane:ethyl acetate 5:1): Rf=0.29.
NMR: $\delta$=4.7–4.5 (1H, m), 4.0–3.2 (4H, m).

In the same manner, the following compound was obtained from the compounds of Reference Example 5(a).

(a) (2α)-2-[2-(Tetrahydropyran-2-yloxy)ethyl]-6,6-dimethyl-norpinan-3-one

TLC (cyclohexane:ethyl acetate=5:1): Rf=0.30.
NMR: $\delta$=4.4 (1H, m), 1.3 (3H, s), 0.87 (3H, s).

Reference Example 7

(2α)-2-[3-Oxa-7-(tetrahydropyran-2-yloxy)heptyl]-6,6-dimethyl-norpinan-3-one

To a solution of 9.89 g of the hydroxy compound [prepared in Reference Example 5(b)] in 200 ml of acetone was added dropwise Jones' reagent with stirring under ice-cooling until the reaction mixture turned to orange. After stirring for few minutes, isopropyl alcohol was added thereto to decompose an excess of oxidizing agent and the mixture was filtered decanted. The solution was neutralized with sodium bicarbonate and was filtered. The filtrate was concentrated under reduced pressure. The mixture thus obtained was dissolved into ethyl acetate, washed successively with a saturated sodium bicarbonate aqueous solution and a saturated sodium chloride aqueous solution, dried over anhydrous magnesium sulfate and concentrated under reduced pressure to obtain 7.1 g of the title compound.

TLC (cyclohexane:ethyl acetate=7:3): Rf=0.52.
NMR: $\delta$=4.57-4.40 (1H, m), 4.00-3.10 (8H, m), 1.28 (3H, s), 0.85 (3H, s).
MS: m/e=338(M+), 254, 223, 181, 165, 85.

Reference Example 8

(2α,3α)-2-[2-(Tetrahydropyran-2-yloxy)ethyl]-3-hydroxy-norpinane 10.2 ml of 25% (w/v) solution of diisobutylaluminium hydride in toluene was added dropwise to a solution of 7.92 g of 2,6-di-tertbutyl-4-methylphenol in 30 ml of toluene at 0° C. under a nitrogen atmosphere, followed by stirring at room temperature for 1 hour. A solution of 428 mg of the norpinan-2-one compound (prepared in Reference Example 6) in 5 ml of toluene was added dropwise thereto under ice-cooling, followed by stirring at a temperature of 0°-10° C. for 30 minutes. The reaction mixture was treated with water, and filtered, and the filtrate was concentrated under reduced pressure. The residue was purified by silica gel column chromatography using a mixture of cyclohexane and ehtyl acetate (2:1) as an eluent to obtain 374 mg of the title compound.

TCL (benzene:ethyl acetate=5:1): Rf=0.26.
NMR: $\delta$=4.90-4.55 (2H, m).

In the same manner, the following compound was obtained from the compound of Reference Example 7.

(a) (2α,3α)-2-[3-Oxa-7-(tetrahydropyran-2-yloxy)-heptyl]-3-hydroxy-6,6-dimethylnorpinane TLC (benzene:ethyl acetate=7:3): Rf=0.57.
NMR: $\delta$=4.60-4.13 (2H, m), 4.03-3.00 (8H, m), 1.15 (3H, s), 1.00 (3H, s).
MS: m/e=340(M+), 322, 297, 256, 213, 187, 85.

Reference Example 9

(2α,3α)-2-[2-(Tetrahydropyran-2-yloxy)ethyl]-3-hydroxy-6,6-dimethylnorpinane 16.53 g of sodium borohydride was added to a solution of 11.559 g of the norpinan-2-one compound [prepared in Reference Example 6 (a)] in 200 ml of methanol at 0° C. under a nitrogen atmosphere, followed by stirring at the same temperature for 2 hours. The reaction mixture was neutralized with acetic acid and concentrated under reduced pressure. The residue was dissolved in diethyl ether, washed with water, dried over anhydrous magnesium sulfate and concentrated under reduced pressure to obtain 9.858 g of the title compound.

TLC (benzene:ethyl acetate=5.1): Rf=0.38.
NMR: $\delta$=4.4 (1H, m), 1.15 (3H, s), 1.0 (3H, s).

Reference Example 10

(2α,3α)-2-[2-(Tetrahydropyran-2-yloxy)ethyl]-3-methanesulfonyloxynorpinane 0.18 ml of methanesulfonyl chloride was added dropwise to a mixture of 374 mg of the 3-hydroxy compound (prepared in Reference Example 8), 10 ml of methylene chloride and 0.45 ml of triethylamine at −20° C. under a nitrogen atmosphere, followed by stirring at the same temperature for 15 minutes. The reaction mixture was diluted with diethyl ether, washed successively with water, a saturated ammonium chloride aqueous solution and a saturated sodium chloride aqueous solution, dried over anhydrous magnesium sulfate and concentrated under reduced pressure to obtain 483 mg of the title compound.

TLC (cyclohexane:ethyl acetate 2:1) Rf=0.29.

In the same manner, the following compounds were obtained from the compounds of Reference Example 9 and Reference Example 8(a).

(a) (2α,3α)-2-[2-(Tetrahydropyran-2-yloxy)ethyl]-3-methanesulfonyloxy-6,6-dimethylnorpinane TLC (cyclohexane:ethyl acetate=2:1): Rf=0.31.

(b) (2α,3α)-2-[3-Oxa-7-(tetrahydropyran-2-yloxy)-heptyl]-3-methansulfonyloxy-6,6-dimethylnorpinane TLC (cyclohexane=ethyl acetate=7:3): Rf=0.42.
NMR: $\delta$=4.67-4.33 (1H, m), 2.95 (3H, s), 1.18 (3H, s), 1.00 (3H, s).
IR: $\nu$=2930, 1350, 1170, 1110, 1030 cm$^{-1}$.

Reference Example 11

(2α,3β)-2-[2-(Tetrahydropyran-2-yloxy)ethyl]-3-azidonorpinane 483 mg of sodium azide was added to a solution of 483 mg of the methanesulfonyloxy compound (prepared in Reference Example 10) in 7.5 ml of hexamethylphosphamide (HMPA) under a nitrogen atmosphere, followed by stirring at 50° C. for 30 minutes. The reaction mixture was diluted with diethyl ether, washed with water, dried over anhydrous magnesium sulfate and concentrated under reduced pressure. The residue was purified by silica gel column chromatography using a mixture of cyclohexane and ethyl acetate (10:1) as an eluent to obtain 342 mg of the title compound.

TLC (cyclohexane:ethyl acetate=10:1): Rf=0.31.
NMR: $\delta$=4.7-4.5 (1H, m), 4.0-3.65 (2H, m), 3.65-3.2 (3H, m).

In the same manner, the following compounds were obtained from the compounds of Reference Example 10(a) and 10(b).

(a) (2α,3β)-2-[2-(Tetrahydropyran-2-yloxy)ethyl]-3-azido-6,6-dimethylnorpinane

TLC (cyclohexane:ethyl acetate=20:1): Rf=0.24.
NMR: $\delta$=4.4 (1H, m), 1.2 (3H, s), 0.93 (3H, s).

(b) (2α,3β)-2-[3-Oxa-7-(tetrahydropyran-2-yloxy)-heptyl]-3-azide-6,6-dimethylnorpinane TLC (cyclohexane:ethyl acetate=7:3): Rf=0.65.
NMR: $\delta$=4.63-4.37 (1H, m), 4.06-3.10 (8H, m), 1.18 (3H, s), 0.91 (3H, s).
MS: m/e=337(M+-N$_2$), 322, 264, 252, 238, 221, 85.

Reference Example 12

(2α,3β)-2-[2-(Tetrahydropyran-2-yloxy)ethyl]-3-aminonorpinane

A mixture of 342 mg of the azide compound (prepared in Reference Example 11), 49 mg of lithium aluminium hydride and 10 ml of diethyl ether was heated under reflux for 30 minutes under a nitrogen atmosphere. The reaction mixture was treated with a 3 N sodium hydroxide aqueous solution and extracted with diethyl ether. The extract was dried over anhydrous magnesium sulfate and concentrated under reduced pressure to obtain 299 mg of the title compound.

IR: $\nu=3375, 2950, 1035$ cm$^{-1}$.

MS: m/e=239 (M+), 197, 166, 154, 148, 95, 85.

In the same manner, the following compounds were obtained from the compounds of Reference Example 11(a) and 11(b).

(a) (2α,3β)-2-[2-(Tetrahydropyran-2-yloxy)ethyl]-3-amino-6,6-dimethylnorpinane

TLC (diethyl ether): Rf=0.00.

(b) (2α,3β)-2-[3-Oxa-7-(tetrahydropyran-2-yloxy)-heptyl]-3-amino-6,6-dimethylnorpinane NMR: δ=4.63–4.42 (1H, m), 4.00–2.93 (8H, m), 1.18 (3H, s), 0.93 (3H, s).

IR: $\nu=3650-2550, 2920, 1450, 1310, 1200, 1120, 1030$ cm$^{-1}$.

MS: m/e=339(M+), 322, 254, 238, 195, 166, 85.

Reference Example 13

(2α,3β)-2-[2-(Tetrahydropyran-2-yloxy)ethyl]-3-trifluoroacetylaminonorpinane 0.66 ml of trifluoroacetic anhydride was added dropwise to a mixture of 299 mg of the amino compound (prepared in Reference Example 12) in 10 ml of methylene chloride and 1 ml of pyridine at 0° C. under a nitrogen atmosphere, followed by stirring at the same temperature for 15 minutes. The reaction mixture was diluted with diethyl ether, washed with water, dried over anhydrous magnesium sulfate and concentrated under reduced pressure. The residue was purified by silica gel column chromatography using a mixture of cyclohexane and ethyl acetate (10:1) as an eluent to obtain 418 mg of the title compound.

TLC (cyclohexane:ethyl acetate=4:1): Rf=0.28.

Melting Point: 65°–70° C.

NMR: δ=4.3–3.2 (5H, m).

In the same manner, the following compounds were obtained from the compounds of Reference Example 12(a) and 12(b).

(a) (2α,3β)-2-[2-(Tetrahydropyran-2-yloxy)ethyl]-3-trifluoroacetylamino-6,6-dimethylnorpinane TLC (cyclohexane:ethyl acetate=4:1): Rf=0.36.

NMR: δ=4.55–4.4 (1H, m), 4.4–4.05 (1H, m), 1.24 (3H, s), 1.02 (3H, s).

(b) (2α,3β)-2-[3-Oxa-7-(tetrahydropyran-2-yloxy)-heptyl]-3-trifluoroacetylamino-6,6-dimethylnorpinane NMR: δ=6.97–6.50 (1H, m), 4.63–4.36 (1H, m), 1.23 (3H, s), 1.00 (3H, s).

IR: $\nu=3300, 2920, 1690, 1540, 1440, 1360$ cm$^{-1}$.

MS: m/e=435(M+), 351, 334, 281, 262, 238, 85.

Reference Example 14

(2α,3β)-2-(2-Hydroxy)ethyl-3-trifluoroacetylaminonorpinane

A mixture of 418 mg of the tetrahydropyran-2-yloxy compound (prepared in Reference Example 13), 10 ml of methanol and a catalytic amount of p-toluenesulfonic acid was stirred at room temperature for 30 minutes under a nitrogen atmosphere. 0.1 ml of triethylamine was added thereto, and the mixture was concentrated under reduced pressure to obtain 292 mg of the title compound.

TLC (cyclohexane:ethyl acetate 1:1): Rf=0.37.

IR (KBr tablet method): $\nu=3400, 3320, 3080, 2950, 1690, 1550$ cm$^{-1}$.

In the same manner, the following compounds were obtained from the compounds of Reference Example 13(a) and 13(b).

(a) (2α,3β)-2-(2-Hydroxy)ethyl-3-trifluoroacetylamino-6,6-dimethylnorpinane

TLC (cyclohexane:ethyl acetate=1:1): Rf=0.38.

NMR: δ=4.55–4.1 (1H, m), 3.62 (2H, t), 1.25 (3H, s), 1.05 (3H, s).

(b) (2α,3β)-2-(3-Oxa-7-hydroxyheptyl)-3-trifluoroacetylamino-6,6-dimethylnorpinane TLC (cyclohexane:ethyl acetate=1:1): Rf=0.51.

NMR: δ=7.26–6.67 (1H, m), 4.50–3.83 (1H, m), 1.23 (3H, s), 1.00 (3H, s).

MS: m/e=351(M+), 333, 320, 276, 235, 207, 189.

Reference Example 15

(2α,3β)-2-Formylmethyl-3-trifluoroacetylaminonorpinane

A solution of 928 mg of sulfuric anhydride-pyridine complex in 20 ml of dimethyl sulfoxide was added dropwise to a mixture of 292 mg of the hydroxy compound (prepared in Reference Example 14) in 20 ml of dimethyl sulfoxide and 1.6 ml of triethylamine at room temperature under a nitrogen atmosphere, followed by stirring at room temperature for 15 minutes. The reaction mixture was poured into ice-water and extracted with a mixture of diethyl ether and ethyl acetate (1:1), and the extract was washed with a saturated sodium chloride aqueous solution, dried over anhydrous magnesium sulfate and concentrated under reduced pressure. The residue was purified by silica gel column chromatography using a mixture of cyclohexane and ethyl acetate (4:1) as an eluent to obtain 206 mg of the title compound.

TLC (cyclohexane:ethyl acetate=2:1): Rf=0.46.

NMR: δ=9.76 (1H, m), 4.4–3.9 (1H, m).

In the same manner, the following compound was obtained from the compound of Reference Example 14(a).

(a) (2α,3β)-2-Formylmethyl-3-trifluoroacetylamino-6,6-dimethylnorpinane

TLC (cyclohexane:ethyl acetate=2:1): Rf=0.44.

NMR: δ=9.73 (1H, broad s), 4.5–4.1 (1H, m), 1.25 (3H, s), 1.05 (3H, s).

Reference Example 16

(Z)-(2α,3β)-2-(6-Methoxycarbonyl-2-hexenyl)-3-trifluoroacetylaminonorpinane 1.524 g of sodium hydride (content: 63%) suspended in 20 ml of dimethyl sulfoxide was stirred at 70° C. for 1 hour under a nitrogen atmosphere. The mixture was added dropwise to a solution of 2.215 g of 4-carboxybutyltriphenylphosphonium bromide in 10 ml of dimethyl sulfoxide at room temperature, followed by stirring for 15 minutes. A solution of 206 mg of the formyl compound (prepared in Reference Example 15) in 5 ml of dimethyl sulfoxide was added dropwise thereto, followed by stirring at room temperature for 30 minutes. The reaction mixture was poured into ice-water, made acidic with oxalic acid and extracted with a mixture of ethyl acetate and diethyl ether (1:1). The extract was dried over anhydrous magnesium sulfate and concentrated under reduced pressure to obtain (Z)-(2α,3β)-2-(6-carboxy-2-hexenyl)-3-trifluoroacetylaminonorpinane having the following physical property.

TLC (cyclohexane:ethyl acetate=1:2): Rf=0.38.

The resulting carboxylic acid was dissolved in a small amount of methanol, and diazomethane-etherate was added thereto until the reaction mixture turned to pale yellow, followed by concentration under reduced pressure. The residue was purified by silica gel column chromatography using a mixture of cyclohexane and ethyl acetate (4:1) as an eluent to obtain 275 mg of the title compound.

TLC (cyclohexane:ethyl acetate=2:1): Rf=0.48.

NMR: $\delta$=5.5–5.3 (2H, m), 4.3–4.0 (1H, m), 3.66 (3H, s).

In the same manner, the following compound was obtained from the compound of Reference Example 15(a).

(a) (Z)-(2α,3β)-2-(6-Methoxycarbonyl-2-hexenyl)-3-trifluoroacetylamino-6,6-dimethylnorpinane TLC (cyclohexane:ethyl acetate=2:1): Rf=0.49.

NMR: $\delta$=5.45–5.3 (2H, m), 4.5–4.1 (1H, m), 3.67 (3H, s), 1.24 (3H, s), 1.07 (3H, s).

(Z)-(2α,3β)-2-(6-Carboxy-2-hexenyl)-3-trifluoroacetylamino-6,6-dimethylnorpinane showed the following physical property.

TLC (cyclohexane:ethyl acetate 1:2): Rf=0.42.

In the same manner, the following compound was obtained from the compound of Reference Example 15(a), 4-carboxybenzyltriphenylphosphonium bromide and diazoethane.

(b) (EZ)-(2α,3β)-2-[3-(4-ethoxycarbonylphenyl)-2-propenyl]-3-trifluoroacetylamino-6,6-dimethylnorpinane NMR: $\delta$=8.08–7.88 (2H, m), 7.44–7.06 (2H, m), 6.60–6.20 (2H, m).

IR: $\nu$=3300, 1710, 1600 cm$^{-1}$.

Reference Example 17

(2α,3β)-2-(6-Methoxycarbonylhexyl)-3-trifluoroacetylamino-6,6-dimethylnorpinane 330 mg of the trifluoroacetylamino compound [prepared in Reference Example 16(a)] were hydrogenated at a pressure of one atmosphere in 10 ml of methanol containing 27 mg of 5% palladium on carbon. The reduction was stopped after the absorption of one equivalent of hydrogen gas. The catalyst was filtered off, and the filtrate was concentrated under reduced pressure to give 283 mg of the title compound.

NMR: $\delta$=6.8 (1H, m), 4.4 (1H, m), 3.7 (3H, s), 1.22 (3H, s), 0.92 (3H, s).

Reference Example 18

(Z)-(2α,3β)-2-(6-Methoxycarbonyl-2-hexenyl)-3-aminonorpinane

A mixture of 258 mg of the trifluoroacetylamino compound (prepared in Reference Example 16) and 2 ml of a 10% (w/v) potassium hydroxide aqueous solution was heated under reflux for 8 hours. The reaction mixture was rendered acidic with 10% hydrochloric acid, and an excess of aqueous ammonia was added thereto, followed by filtration. The filtrate was concentrated to obtain (Z)-(2α,3β)-(6-carboxy-2-hexenyl)-3-amononorpinane. This was dissolved in a small amount of methanol, and diazomethane-etherate was added thereto until the reaction mixture was coloured in pale yellow, followed by concentration under reduced pressure to obtain 160 mg of the title compound.

IR: $\nu$=2930, 1740, 1435 cm$^{-1}$.

NMR: $\delta$=5.55–5.3 (2H, m), 3.67 (3H, s), 3.1–2.7 (1H, m).

MS: m/e=251 (M+), 220, 209, 183, 164.

In the same manner, the following compounds were obtained from the compounds of Reference Example 16(a) and 16(b) and Reference Example 17.

(a) (Z)-(2α,3β)-2-(6-Methoxycarbonyl-2-hexenyl)-3-amino-6,6-dimethyl-norpinane.

IR: $\nu$=1740 cm$^{-1}$.

NMR: $\delta$=5.6–5.2 (2H, m), 3.67 (3H, s), 3.3–3.0 (1H, m), 1.2 (3H, s), 0.99 (3H, s).

(b) (EZ)-(2α,3β)-2-[3-(4-methoxycarbonylphenyl)-2-propenyl]-3-amino-6,6-dimethylnorpinane NMR: $\delta$=8.0–7.8 (2H, m), 7.44–7.06 (2H, m), 6.6–6.2 (2H, m), 3.65 (3H, s).

IR: $\nu$=3300, 1710, 1600 cm$^{-1}$.

(c) (2α,3β)-2-(6-methoxycarbonylhexyl)-3-amino-6,6-dimethylnorpinane

NMR: $\delta$=3.6 (3H, s), 1.2 (3H, s), 0.92 (3H, s).

MS: m/e=264(M+-17), 250, 238, 212, 185.

Reference Example 19

(2α,3β)-2-(3-Oxa-6-carboxyhexyl)-3-trifluoroacetylamino-6,6-dimethylnorpinone

To a solution of 2.01 g of the hydroxy compound [prepared in Reference Example 14(b)] in 100 ml of acetone was added dropwise Jones' reagent with stirring under ice-cooling until the reaction mixture turned to orange. Isopropyl alcohol was added thereto to decompose an excess of oxidizing agent and the mixture was decanted. The solution was concentrated, and dissolved into ethyl acetate and then washed successively with water and a saturated sodium chloride aqueous solution, dried over anhydrous magnesium sulafte, and concentrated under reduced pressure to obtain 2.02 g of the title compound.

NMR: $\delta$=9.77–9.22 (1H, m), 7.03–6.63 (1H, m), 4.52–3.90 (1H, m), 1.23 (3H, s), 1.00 (3H, s).

IR: $\nu$=3300, 2920, 1700, 1650, 1360, 1100, 900, 735 cm$^{-1}$.

MS: m/e=365(M+), 347, 298, 278, 252, 192.

Reference Example 20

(2α,3β)-2-(3-Oxa-6-methoxycarbonylhexyl)-3-amino-6,6-dimethylnorpinane 917 mg of the title compound was prepared from 2.02 g of the compound of Reference Example 19 by the same manner as described in Reference Example 18.

TLC (chloroform:tetrahydrofuran:formic acid=5:2:1): Rf=0.52.

NMR: $\delta$=3.60 (3H, s), 1.18 (3H, s), 0.93 (3H, s).

MS: m/e=283(M+), 252, 222, 201, 187, 122.

EXAMPLE 1

(5Z,15ξ)-9,11-Methano-10,10-dimethyl-13-aza-15-hydroxy-11a-carbathromb-5-enoic acid methyl ester 100 mg of 1-heptylene oxide was added dropwise to a solution of 203 mg of the amino compound [prepared in Reference Example 18(a)] in 5 ml of methanol under ice-cooling, and the mixture was stirred at 50° C. for 4 hours, followed by refluxing for 3.5 hours. The resulting reaction mixture was concentrated under reduced pressure, and the residue was purified by silica gel column chromatography using a mixture of chloroform and methanol (95:5) as an eluent to obtain 163 mg of the title compound as an isomeric mixture at the C-15 position. This was further developed twice with methanol using a separative TLC plate to separate the isomers at the 15-position.

(a) 15β-Hydroxy isomer of the title compound. Yield: 32 mg.

TLC (methanol): Rf=0.52.

IR: ν=2920, 1735, 1440, 1360 cm⁻¹.

NMR: δ=5.60–5.23 (2H, m), 3.60 (3H, s), 1.20 (3H, s), 0.96 (3H, s).

MS: m/e=393 (M+), 362, 322, 306.

(b) 15α-hydroxy isomer of the title compound. Yield: 28 mg.

TLC (methanol): Rf=0.47.

IR: ν=2910, 1735, 1450, 1360 cm⁻¹.

NMR: δ=5.60–5.23 (2H, m), 3.60 (3H, s), 1.20 (3H, s), 0.96 (3H, s).

MS: m/e=393 (M+), 362, 322, 306.

EXAMPLE 2

(5Z,15β)-9,11-Methano-10,10-dimethyl-13-aza-15-hydroxy-11a-carbathromb-5-enoic acid 32 mg of the methyl ester obtained in Example 1(a) was dissolved in 1 ml of a mixture of water and methanol (1:1), and 10 mg of lithium hydroxide was added thereto, followed by stirring at 50° C. for 2 hours. After the methanol was distilled off, the residue was neutralized with acetic acid. The white solid thus obtained was washed with water, dissolved in chloroform and hexane was added thereto for recrystallization, thereby to obtain 16.6 mg of the title compound. TLC (methylene chloride:tetrahydrofuran:acetic acid=5:1:1): Rf=0.61.

IR (KBr tablets): ν=2920, 1550, 1440, 1390 cm⁻¹.

NMR: δ=5.56–5.27 (2H, m), 4.11–3.78 (1H, m), 1.25 (3H, s), 0.96 (3H, s), 0.85 (3H, t).

MS: m/e=379 (M+), 362, 338.

In the same manner, the following compound was obtained from the compound of Example 1(b).

(a) (5Z,15α)-9,11-Methano-10,10-dimethyl-13-aza-15-hydroxy-11a-carbathromb-5-enoic acid TLC (methylene chloride:tetrahydrofuran:acetic acid=5:1:1): Rf=0.55.

IR (KBr tablets): ν=2920, 1550, 1440, 1390 cm⁻¹.

NMR: δ=5.55–5.28 (2H, m), 4.21–3.83 (1H, m), 3.58–3.24 (1H, m), 1.24 (3H, s), 0.98 (3H, s), 0.85 (3H, t).

MS: m/e=397 (M+), 362, 338.

EXAMPLE 3

The following compounds having the below structure were obtained from the compound of Reference Example 18(a) and the corresponding epoxide compounds of the general formula VIII by the same manner as described in Example 1 and 2.

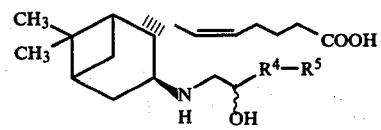

| Example No. | $R^4$—$R^5$ | Isomer | NMR | IR (KBr methods) | MS |
|---|---|---|---|---|---|
| (a) | n-hexyl | 15β-isomer | 8.28(3H;b), 5.43(2H,m), 3.94(1H,m), 3.35(1H,m), 3.08(1H,m), 1.23(3H,s), 0.96(2H,s), 0.87(3H,t) | 2300–3600, 3370, 1620, 1540, | 393(M+), 392, 378, 376, 324, 308, 297, 278 |
|  |  | 15α-isomer | 8.40(3H,b), 5.43(2H,m), 4.00(1H,m), 3.40(1H,m), 2.91(2H,m), 1.23(3H,s), 0.98(3H,s), 0.87(3H,t) | 2300–3600, 3300, 1620, 1540 | identical to the data of 15β-isomer |
| (b) | n-heptyl | 15β-isomer | 8.53(3H,b), 5.40(2H,m), 3.94(1H,m), 3.35(1H,m), 3.08(1H,m), 1.24(3H,s), 0.96(3H,s), 0.87(3H,t) | 2300–3600, 3370, 1610, 1540 | 407(M+), 406, 392, 390, 366, 338, 311, 308, 278 |
|  |  | 15α-isomer | 8.68(3H,b), 5.42(2H,m), 4.00(1H,m), 3.40(1H,m), 2.92(1H,m), 1,23(3H,s), 0.98(3H,s), 0.87(3H,t) | 2300–3600, 1610, 1540 | identical to the data of 15β-isomer |
| (c) | n-octyl | 15β-isomer | 8.62(3H,b), 5.42(2H,m), 3.93(1H,m), 3.85(1H,m), 3.08(1H,m), 0.96(3H,s), 0.87(3H,t) | 2300–3600, 3350, 1620, 1540 | 421(M+), 420, 406, 404, 352, 325, 308, 278 |
|  |  | 15α-isomer | 8.48(3H,b), 5.43(2H,m), 4.00(1H,m), 3.44(1H,m), 2.92(1H,m), 0.98(3H,s), 0.87(3H,t) | 2300–3600, 1620, 1550 | identical to the data of 15β-isomer |
| (d) | ~~~~≡~~CH₃ | 15β-isomer | 8.70(3H,b), 5.40(2H,m), 4.10(1H,m), 3.40(1H,m), 2.90(1H,m), 0.88, 0.94 and 0.97 (Me signal not assign) | 2300–3600, 3350, 1620, 1540 | 421(M+), 420, 406, 380, 352, 325, 328, 278 |
|  |  | 15α-isomer | 8.7((3H,b), 5.40(2H,m), 4.05(1H,m), 3.35(1H,m), 0.96(3H,s), 0.83, 0.87 and 0.89 (Me signal) | 2300–3600, 3250, 1620, 1540 | identical to the data of 15β-isomer |
| (e) | ~~S~~~~~ | 15β-isomer | 8.5–8.2(3H,m), 5.6–5.35(2H,m), 4.4–4.0(2H,m), 3.55–3.20(2H,m), 1.24(3H,s), 0.98(3H,s), 1.05–0.78 (3H,m) | 3600–3200, 2920, 2850, 1615, 1530, 1390 | 425(M+), 408, 329, 322, 278 |
|  |  | 15α-isomer | 9.0–8.7(3H,m), 5.6–5.33(2H,m), 4.4–4.05(1H,m), 3.6–3.0(2H,m), 1.24 (3H,s), 0.99(3H,s), 1.05–0.79(3H,m) | 3600–3100, 2920, 2850, 1620, 1540, 1390 | identical to the data of 15β-isomer |

-continued

| Example No. | R⁴—R⁵ | Isomer | NMR | IR (KBr methods) | MS |
|---|---|---|---|---|---|
| (f) | CH₂–C₆H₅ | 15β-isomer | 8.74(3H,b), 7.20(5H,s), 5.40(2H,m), 4.13(1H,m), 3.22(1H,m), 1.20(3H,s), 0.90(3H,s) | 2300–3600, 3370, 1620, 1540, 740, 690 | 399(M⁺), 398, 384, 382, 358, 330, 308, 303, 278 |
| | | 15α-isomer | 7.95(3H,b), 7.23(5H,s), 5.40(2H,m), 4.31(1H,m), 3.22(1H,m), 1.19(3H,s), 0.88(3H,s) | 3600–2300, 1620, 1540, 740, 690 | identical to the data of 15β-isomer |
| (g) | CH₂–O–C₆H₅ | 15β-isomer | 7.40–6.79(5H,m), 5.56–5.29(2H,m), 4.68–4.44(1H,m), 4.20–3.80(2H,m), 1.22(3H,s), 0.90(3H,s) | 2930, 1600, 1560, 1500, 1400, 1245, 755, 690 | 415(M⁺), 346, 319 |
| | | 15α-isomer | 7.37–6.77(5H,m), 5.54–5.28(2H,m), 4.70–4.29(1H,m), 4.23–3.69(2H,m), 1.22(3H,s), 0.95(3H,s) | 2920, 1600, 1570, 1500, 1400, 1240, 750, 690 | identical to the data of 15β-isomer |
| (h) | CH₂–O–C₆H₄–CH₃ | 15β-isomer | 8.7(3H,b), 7.15–6.65(4H,m), 5.45 (2H,m), 4.45(1H,m), 3.95(2H,m), 2.26(3H,s), 1.21(3H,s), 0.94(3H,s) | 3650–2300, 1615, 1510, 1400, 810 | 429(M⁺), 428, 414, 412, 388, 360, 333, 322, 278 |
| | | 15α-isomer | 8.8(3H,b), 7.15–6.7(4H,m), 5.4 (1H,m), 4.45(1H,m), 3.9(2H,m), 2.27(3H,s), 1.21(3H,s), 0.95(3H,s) | 3600–2300, 1615, 1510, 1400, 820 | identical to the data of 15β-isomer |
| (i) | CH₂–O–C₆H₄–C₂H₅ | 15β-isomer | 8.9(3H,b), 7.2–6.7(4H,m), 5.45 2H,m), 4.45(1H,m), 4.0(2H,m), 1.22(3H,s), 1.19(3H,t), 0.95(3H,s) | 3600–2500, 1610, 1510, 1400, 820 | 443(M⁺), 442, 428, 426, 374, 347, 322, 308, 278, |
| | | 15α-isomer | 8.4(3H,b), 7.2–6.7(4H,m), 5.4 (2H,m), 4.5(1H,m), 4.0(2H,m), 1.23(3H,s), 1.19(3H,t), 0.95(3H,s) | 3600–2300, 1610, 1510, 1400, 820 | identical to the data of 15β-isomer |
| (j) | CH₂–O–C₆H₄–C₃H₇ | 15β-isomer | 8.9(3H,b), 7.15–6.7(4H,m), 5.4 (2H,m), 4.45(1H,m), 4.0(2H,m), 1.21(3H,s), 0.94(3H,s), 0.91(3H,t) | 3500–3200, 2940, 1610, 1510, 1400, 1250 | 457(M⁺), 456, 442, 440, 416, 388, 361, 322, 308, 278 |
| | | 15α-isomer | 8.45(3H,b), 7.15–6.7(4H,m), 5.4 (2H,m), 4.5(1H,m), 4.0(2H,m), 1.23(3H,s), 0.95(3H,s), 0.91(3H,t), | 3600–2300, 1610, 1550, 1510, 1400, 1245 | identical to the data of 15β-isomer |
| (k) | CH₂–O–C₆H₄–Cl | 15β-isomer | 9.05(3H,b), 7.26–6.7(4H,m), 5.45 (2H,m), 4.45(1H,m), 3.95(2H,m), 1.22(3H,s), 0.95(3H,s) | 3500–3200, 2930, 1620, 1490, 1400, 1240, 820 | 449(M⁺), 448, 434, 432, 408, 380, 353, 322, 308, 278 |
| | | 15α-isomer | 9.05(3H,b), 7.26–6.7(4H,m), 5.45 (2H,m), 4.45(1H,m), 4.0(2H,m), 1.22(3H,s), 0.96(3H,s) | 3650–2300, 1550, 1490, 1400, 1245, 820 | identical to the data of 15β-isomer |
| (l) | CH₂–O–C₆H₄–Cl (meta) | 15β-isomer | 8.9(3H,b), 7.2–6.7(4H,m), 5.4 (2H,m), 4.45(1H,m), 4.0(2H,m), 1.22(3H,s), 0.95(3H,s) | 3600–2300, 1600, 1550, 1480, 1400, 1280, 1230, 1040, 760 | 449(M⁺), 448, 434, 432, 408, 380, 353, 322, 308, 278 |
| | | 15α-isomer | 8.6(3H,b), 7.2–6.7(4H,m), 5.4 (2H,m), 4.5(1H,m), 4.0(2H,m), 1.23(3H,s), 0.96(3H,s) | 3600–2300, 1590, 1540, 1480, 1400, 1280, 1250, 1040, 770 | identical to the data of 15β-isomer |
| (m) | CH₂–O–C₆H₄–CF₃ | 15β-isomer | 8.5(3H,b), 7.5–6.95(4H,m), 5.45 (2H,m), 4.45(1H,m), 4.05(2H,m), 1.23(3H,s), 0.95(3H,s) | 3650–2300, 1620, 1590, 1520, 1450, 1330, 1160, 1120, 1060, 880, 780 | 483(M⁺), 482, 468, 464, 442, 414, 387, 322, 308, 278 |
| | | 15α-isomer | 8.6(3H,b), 7.5–6.95(4H,m), 5.45 (2H,m), 4.55(1H,m), 4.1(2H,m), 1.23(3H,s), 0.96(3H,s) | 3600–2300, 1590, 1550, 1490, 1440, 1320, 1160, 1120, 1060, 880, 790 | identical to the data of 15β-isomer |
| (n) | CH₂–S–C₆H₅ | 15β-isomer | 7.45–7.1(5H,m), 5.54–5.22(2H,m), 4.32–4.00(1H,m), 1.22(3H,s), 0.94 (3H,s) | 2920, 1540, 1400, 740, 685 | 431(M⁺), 335 |
| | | 15α-isomer | 7.45–7.1(5H,m), 5.50–5.30(2H,m), 4.40–4.10(1H,m), 1.22(3H,s), 0.93 (3H,s) | 2920, 1550, 1400, 740, 690 | 431(M⁺), 362, 335 |
| (o) | CH₂–S–C₆H₄–CH₃ | 15β-isomer | 8.23(3H,b), 7.41–6.92(4H,m), 5.41 (2H,m), 4.09(1H,m), 2.28(3H,s), 1.21(3H,s), 0.94(3H,s) | 3600–2200, 3330, 2940, 1620, 1540, 1400, 1090, 800 | 445(M⁺), 444, 376, 349, 322, 278 |
| | | 15α-isomer | 7.65(3H,b), 7.38–6.97(4H,m), 5.40 (2H,m), 4.16(1H,m), 2.29(3H,s), 1.22(3H,s), 0.93(3H,s) | 3650–2250, 2940, 1630, 1550, 1490, 1400, 810 | identical to the data of 15β-isomer |

-continued

| Example No. | R⁴—R⁵ | Isomer | NMR | IR (KBr methods) | MS |
|---|---|---|---|---|---|
| (p) | ~S-⟨O⟩-C$_2$H$_5$ | 15β-isomer | 7.60(3H,b), 7.40–7.00(4H,m), 5.40 (2H,m), 4.16(1H,m), 1.22(3H,s), 1.21(3H,t), 0.94(3H,s) | 3600–2250, 2950, 1620, 1540, 1490, 1400, 1090, 820 | 459(M$^+$), 458, 390, 363, 322, 278 |
| | | 15α-isomer | 7.75(3H,b), 7.40–7.00(4H,m), 5.41 (2H,m), 4.17(1H,m), 1.22(3H,s), 1.20(3H,t), 0.93(3H,s) | 3600–2200, 3150, 2920, 1630, 1540, 1490, 1390, 1090, 820 | identical to the data of 15β-isomer |
| (q) | ~S-⟨O⟩-C$_3$H$_7$ | 15β-isomer | 8.00(3H,b), 7.38–6.98(4H,m), 5.41 (2H,m), 4.11(1H,m), 1.22(3H,s), 0.94(3H,s), 0.91(3H,t) | 3600–2300, 2930, 1560, 1490, 1370 | 473(M$^+$), 472, 404, 377, 322, 278 |
| | | 15α-isomer | 7.71(3H,b), 7.40–6.97(4H,m), 5.40 (2H,m), 4.16(1H,m), 1.22(3H,s), 0.93(3H,s), 0.92(3H,t) | 3650–2250, 3400, 2920, 1620, 1550, 1490, 1390 | identical to the data of 15β-isomer |
| (r) | ~S-⟨O⟩-Cl | 15β-isomer | 7.76(3H,b), 7.38–7.13(4H,m), 5.38 (2H,m), 4.16(1H,m), 1.23(3H,s), 0.95(3H,s) | 3650–2250, 3430, 2920, 1550, 1480, 1390, 1090, 820 | 465(M$^+$), 464, 396, 369, 322, 278 |
| | | 15α-isomer | 7.59(3H,b), 7.40–7.12(4H,m), 5.41 (2H,m), 4.17(1H,m), 1.22(3H,s), 0.93(3H,s) | 3600–2300, 3400, 2920, 1560, 1480, 1390, 1100, 820 | identical to the data of 15β-isomer |
| (s) | ~S-⟨O⟩ (Cl meta) | 15β-isomer | 7.38(3H,b), 7.35–7.06(4H,m), 5.41 (2H,m), 4.18(1H,m), 1.23(3H,s), 0.95(3H,s) | 3600–2250, 3330, 2930, 1620, 1590, 1550, 1460, 1400, 790 | 466(M$^+$), 464, 396, 369, 322, 278 |
| | | 15α-isomer | 7.50–7.05(7H,m), 5.39(2H,m), 4.24 (1H,m), 1.23(3H,s), 0.95(3H,s) | 3650–2250, 3430, 2920, 1620, 1580, 1550, 1460, 1400, 790 | identical to the data of 15β-isomer |
| (t) | ~S-⟨O⟩ (CF$_3$ meta) | 15β-isomer | 8.13(3H,b), 7.64–7.12(4H,m), 5.40 (2H,m), 4.18(1H,m), 1.22(3H,s), 0.94(3H,s) | 3650–2250, 3350, 2930, 1620, 1540, 1400, 1320, 1160, 1120, 790, 690 | 499(M$^+$), 498, 430, 403, 322, 278 |
| | | 15α-isomer | 7.58(3H,b), 7.46–7.13(4H,m), 5.39 (2H,m), 4.28(1H,m), 1.22(3H,s), 0.93(3H,s) | 3600–2300, 3400, 2920, 1550, 1400, 1320, 1160, 1120, 790, 690 | identical to the data of 15β-isomer |

EXAMPLE 4

(15ξ)-9,11-Methano-10,10-dimethyl-13-aza-15-hydroxy-16-phenylthio-17,18,19,20-tetranor-11a-carbathrombanoic acid The title compound was prepared from (2α,3β)-2-(6-methoxycarbonylhexyl)-3-amino-6,6-dimethylnorpinane [prepared as Reference Example 18(c)] and phenylglycidyl thioether by the same manner as described in Example 1 and 2.

(a) 15β-Hydroxy isomer of the title compound.
Melting Point: 102°–110° C.
NMR: δ=8.03(3H, b), 7.42–7.07 (5H, m), 4.10 (1H, m), 1.21 (3H, s), 0.90 (3H, s).
IR (KBr method): ν=3650–2250, 3420, 2920, 1550, 1390, 740, 690 cm$^{-1}$.
MS: m/e=433(M$^+$), 432, 362, 337, 280, 237, 209, 184.

(b) 15α-Hydroxy isomer of the title compound.
Melting Point: 133°–137° C.
NMR: δ=8.05 (3H, b), 7.41–7.12 (5H, m), 4.21 (1H, m), 1.21 (3H, s), 0.89 (3H, s).
IR (KBr method): ν=3350–2250, 3380, 2920, 1550, 1390, 740, 690.
MS: m/e=433(M$^+$), 432, 362, 337, 280, 237, 209, 184.

EXAMPLE 5

(15ξ)-5-Oxa-9,11-methano-10,10-dimethyl-13-aza-15-hydroxy-16-(4-ethylphenyl-thio)-17,18,19,20-tetranor-11a-carbathrombanoic acid The title compound was prepared from (2α,3β)-2-(3-oxa-6-methoxycarbonylhexyl)-3-amino-6,6-dimethylnorpinane (prepared as Reference Example 20) and (4-ethylphenyl)glycidyl thioether by the same manner as described in Example 1 and 2.

(a) 15β-Hydroxy isomer of the title compound.
Melting Point: 74°–84° C.
NMR: δ=8.80–8.31 (3H, m), 7.40–6.96 (4H, m), 4.45–4.10 (1H, m), 2.75–2.46 (2H, q), 1.32–1.11 (3H, t), 1.21 (3H, s), 0.89 (3H, s).
IR (KBr method): ν=3560–2200, 3420, 2920, 1620, 1550, 1490, 1390, 1090, 820 cm$^{-1}$.
MS: m/e=463(M$^+$), 445, 394, 376, 367, 282.

(b) 15α-Hydroxy isomer of the title compound.
Melting Point: 124°–129° C.
NMR: δ=9.62–9.10 (3H, m), 7.43–6.95 (4H, m), 4.36–3.96 (1H, m), 2.74–2.45 (2H, q), 1.33–1.09 (3H, t), 1.22 (3H, s), 0.89 (3H, s).
IR (KBr method): ν=3350–2200, 3200, 2920, 1550, 1490, 1400, 1100, 820 cm$^{-1}$.
MS: m/e=463(M$^+$), 445, 394, 376, 367, 282.

EXAMPLE 6

(5EZ,15ξ)-1,5-Inter-p-phenylene-9,11-methano-10,10-dimethyl-13-aza-15-hydroxy-16-(4-ethylphenylthio)-2,3,4,17,18,19,20-heptanor-11a-carbathromb-5-enoic acid The title compound was prepared from (EZ)-(2α,3β)-2-[3-(4-methoxycarbonylphenyl-2-propenyl]-3-amino-6,6-dimethylnorpinane [prepared as Reference Example 18(b)] and (4-ethylphenyl)glycidyl thioether by the same manner as described in Example 1 and 2.

(a) 15β-Hydroxy isomer of the title compound.

NMR: δ=8.06–7.80 (2H, m), 7.38–7.02 (6H, m), 6.74–5.50 (2H, m), 1.06 (3H, s), 0.67 (3H, s).

IR (KBr method): ν=3700–2300, 3430, 2920, 1600, 1530, 1490, 1380, 820, 770 cm⁻¹.

MS: m/e=493(M+), 475, 379, 338, 242, 229.

(b) 15α-Hydroxy isomer of the title compound.

NMR: δ=8.08–7.79 (2H, m), 7.39–7.02 (6H, m), 6.72–5.48 (2H, m), 1.08 (3H, s), 0.67 (3H, s).

IR (KBr method): ν=3700–2300, 3430, 2920, 1600, 1530, 1490, 1380, 820, 770 cm⁻¹.

MS: m/e=493(M+), 475, 379, 338, 242, 229.

EXAMPLE 7

(5Z)-9,11-Methano-13-aza-11a-carbathromb-5-enoic acid methyl ester 0.15 ml of heptyl aldehyde was added dropwise to a mixture of 145 mg of the amino compound (prepared in Reference Example 18), 1 g of Molecular Sieves 3 A and 3 ml of methanol at room temperature under a nitrogen atmosphere, followed by allowing the mixture to stand at room temperature for 18 hours. The reaction mixture was filtered, and 23 mg of sodium borohydride was added to the filtrate under ice-cooling, followed by stirring at the same temperature for 1 hour. 1 ml of acetone was added thereto, and the mixture was concentrated under reduced pressure. The residue was dissolved in diethyl ether, washed with a saturated sodium chloride aqueous solution, dried over anhydrous magnesium sulfate and concentrated under reduced pressure. The residue was purified by silica gel column chromatography using a mixture of hexane and diethyl ether (2:1) as an eluent to obtain 114 mg of the title compound.

TLC (methylene chloride:tetrahydrofuran:acetic acid=10:2:1): Rf=0.60.

IR: ν=2930, 1740 cm⁻¹.

NMR: δ=5.6–5.2 (2H, m), 3.66 (3H, m), 1.0–0.7 (3H, m).

EXAMPLE 8

(5Z)-9,11-Methano-13-aza-11a-carbathromb-5-enoic acid

A mixture of 98 mg of the methyl ester (prepared in Example 7) and 2 ml of a 10% (w/v) potassium hydroxide aqueous solution was heated under reflux for 6 hours. The reaction mixture was made acidic with 10% hydroxhloric acid, and an excess of aqueous ammonia was added thereto, followed by filtration. The filtrate was extracted with diethyl ether, and the extract was concentrated under reduced pressure. The residue was recrystallized from diethyl ether and hexane to obtain 51 mg of the title compound.

TLC (methylene chloride:tetrahydrofuran:acetic acid=10:2:1): Rf=0.38.

IR (KBr method): ν=1630, 1560, 1400 cm⁻¹.

NMR: δ=5.6–5.25 (2H, m), 3.3–2.6 (3H, m).

MS: m/e=335(M+), 294, 250, 168, 167.

EXAMPLE 9

(5Z)-9,11-Methano-10,10-dimethyl-13-aza-11a-carbathromb-5-enoic acid

The title compound was prepared from the amino compound of Reference Example 18(a) by the same manner as described in Example 7 and 8.

TLC (methylene chloride:tetrahydrofuran:acetic acid=10:2:1): Rf=0.51.

IR (KBr method): ν=1625, 1545, 1395 cm⁻¹.

NMR (methanol-d₄ solution): δ=5.6–5.3 (2H, m), 1.27 (3H, s), 1.03 (3H, s).

EXAMPLE 10

(5Z)-9,11-Methano-10,10-dimethyl-13-aza-16-phenylthio-17,18,19,20-tetranor-11a-carbathromb-5-enoic acid The title compound was prepared from the amino compound of Reference Example 18(a) and 3-phenylthiopropanal by the same manner as described in Example 7 and 8.

Melting Point: 139°–143° C.

NMR: δ=9.0–8.6 (2H, m), 7.45–7.1 (5H, m), 5.53–5.25 (2H, m), 1.21 (3H, s), 0.94 (3H, s).

IR (KBr method): ν=3600–3100, 2930, 3100–2200, 1620, 1540, 1395, 730, 690 cm⁻¹.

MS: m/e=415(M+), 319, 306, 278.

The following Example illustrate pharmaceutical composition according to the present invention.

EXAMPLE 11

10 g of (5Z,15β)-9,11-methano-10,10-dimethyl-13-aza-15-hydroxy-16-phenylthio-17,18,19,20-tetranor-11a-carbathromb-5-enoic acid, 200 mg of cellulose calcium gluconate (disintegrator), 100 mg of magnesium stearate (lubricant) and 9.7 g of crystalline cellulose were mixed and punched out in a usual manner to obtain tablets each containing 100 mg of the active ingredient.

What we claim:

1. A compound of the general formula:

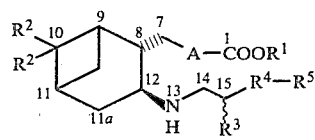

[wherein A represents $-CH_2CH_2-(CH_2)_m-$, (i)

$-CH\overset{cis}{=\!\!=}CH-(CH_2)_m-$, (ii)

$-CH_2-O-(CH_2)_m-$ or (iii)

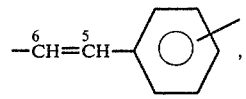

(iv)

(in which m is an integer of 1 to 6, the double bond between the carbon atoms in positions 5 and 6 in (iv) is in cis or trans-configuration or a mixture thereof and the phenylene group in (iv) represents o-, m- or p-phenylene), R¹ represents a hydrogen atom or a straight- or branched-chain alkyl group of 1 to 12 carbon atoms, two R² both represent hydrogen atoms or methyl groups, R³ represents a hydrogen atom or a hydroxy group, R⁴ represents a single bond or a straight- or branched-chain alkylene group of 1 to 5 carbon atoms, R⁵ represents (i) a straight- or branched-chain alkyl, alkoxy or alkylthio group of 1 to 8 carbon atoms, (ii) a cycloalkyl or cycloalkyloxy group of 4 to 7 carbon atoms being unsubstituted or substituted by at least one straight- or branched-chain alkyl group of 1 to 8 carbon atoms or (iii)

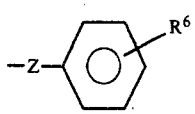

(in which Z represents a single bond, an oxygen atom or a sulfur atom and $R^6$ may occupy any of the free positions on the phenyl ring and represents a hydrogen atom, a halogen atom, a hydroxy group, a straight- or branched-chain alkyl or alkoxy group of 1 to 5 carbon atoms, a trihalomethyl group, an amino group or a mono- or dialkyl-amino group of 1 to 5 carbon atoms) and the wavy line attached to the carbon atom in position 15 represents α- or β-configuration or a mixture thereof, provided that, when $R^3$ represents a hydroxy group and $R^4$ represents a single bond, $R^5$ does not represent an alkoxy group, an alkylthio group, a cycloalkyloxy group, a phenoxy group and a phenylthio group], or cyclodextrin clathrates thereof, or when $R^1$ represents a hydrogen atom, non-toxic salts thereof.

2. A compound according to claim 1 wherein $R^3$ represents a hydroxy group.

3. A compound according to claim 2 wherein two $R^2$ both represent methyl groups.

4. A compound according to claim 3 wherein A represents

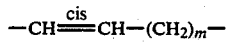

(in which m is as defined in claim 1).

5. A compound according to claim 4 wherein $R^1$ represents a hydrogen atom or a methyl group.

6. A compound according to claim 5 wherein $R^5$ represents a straight- or branched-chain alkyl, alkoxy or alkylthio group of 1 to 8 carbon atoms.

7. A compound according to claim 6 which is (5Z,15ξ)-9,11-methano-10,10-dimethyl-13-aza-15-hydroxy-11a-carbathromb-5-enoic acid or its methyl ester.

8. A compound according to claim 6 which is (5Z,15ξ)-9,11-methano-10,10-dimethyl-13-aza-15-hydroxy-20-methyl-11a-carbothromb-5-enoic acid or its methyl ester.

9. A compound according to claim 6 which is (5Z,15ξ)-9,11-methano-10,10-dimethyl-13-aza-15-hydroxy-20-ethyl-11a-carbathromb-5-enoic acid or its methyl ester.

10. A compound according to claim 6 which is (5Z,15ξ)-9,11-methano-10,10-dimethyl-13-aza-15-hydroxy-20-propyl-11a-carbathromb-5-enoic acid or its methyl ester.

11. A compound according to claim 6 which is (5Z,15ξ)-9,11-methano-10,10-dimethyl-13-aza-15-hydroxy-17-methyl-20-ethyl-11a-carbathromb-5-enoic acid or its methyl ester.

12. A compound according to claim 6 which is (5Z,15ξ)-9,11-methano-10,10-dimethyl-13-aza-15-hydroxy-17-thia-20-ethyl-11a-carbathromb-5-enoic acid or its methyl ester.

13. A compound according to claim 5 wherein $R^5$ represents

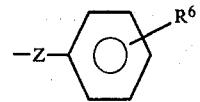

(in which the various symbols are as defined in claim 1).

14. A compound according to claim 13 which is (5Z,15ξ)-9,11-methano-10,10-dimethyl-13-aza-15-hydroxy-16-phenyl-17,18,19,20-tetranor-11a-carbathromb-5-enoic acid or its methyl ester.

15. A compound according to claim 13 which is (5Z,15ξ)-9,11-methano-10,10-dimethyl-13-aza-15-hydroxy-16-phenoxy-17,18,19,20-tetranor-11a-carbathromb-5-enoic acid or its methyl ester.

16. A compound according to claim 13 which is (5Z,15ξ)-9,11-methano-10,10-dimethyl-13-aza-15-hydroxy-16-(4-methylphenoxy)-17,18,19,20-tetranor-11a-carbothromb-5-enoic acid or its methyl ester.

17. A compound according to claim 13 which is (5Z,15ξ)-9,11-methano-10,10-dimethyl-13-aza-15-hydroxy-16-(4-ethylphenoxy)-17,18,19,20-tetranor-11a-carbathromb-5-enoic acid or its methyl ester.

18. A compound according to claim 13 which is (5Z,15ξ)-9,11-methano-10,10-dimethyl-13-aza-15-hydroxy-16-(4-propylphenoxy)-17,18,19,20-tetranor-11a-carbathromb-5-enoic acid or its methyl ester.

19. A compound according to claim 13 which is (5Z,15ξ)-9,11-methano-10,10-dimethyl-13-aza-15-hydroxy-16-(4-chlorophenoxy)-17,18,19,20-tetranor-11a-carbathromb-5-enoic acid or its methyl ester.

20. A compound according to claim 13 which is (5Z,15ξ)-9,11-methano-10,10-dimethyl-13-aza-15-hydroxy-16-(3-chlorophenoxy)-17,18,19,20-tetranor-11a-carbothromb-5-enoic acid or its methyl ester.

21. A compound according to claim 13 which is (5Z,15ξ)-9,11-methano-10,10-dimethyl-13-aza-15-hydroxy-16-(3-trifluoromethylphenoxy)-17,18,19,20-tetranor-11a-carbathromb-5-enoic acid or its methyl ester.

22. A compound according to claim 13 which is (5Z,15ξ)-9,11-methano-10,10-dimethyl-13-aza-15-hydroxy-16-phenylthio-17,18,19,20-tetranor-11a-carbathromb-5-enoic acid or its methyl ester.

23. A compound according to claim 13 which is (5Z,15ξ)-9,11-methano-10,10-dimethyl-13-aza-15-hydroxy-16-(4-methylphenylthio)-17,18,19,20-tetranor-11a-carbathromb-5-enoic acid or its methyl ester.

24. A compound according to claim 13 which is (5Z,15ξ)-9,11-methano-10,10-dimethyl-13-aza-15-hydroxy-16-(4-ethylphenylthio)-17,18,19,20-tetranor-11a-carbathromb-5-enoic acid or its methyl ester.

25. A compound according to claim 13 which is (5Z,15ξ)-9,11-methano-10,10-dimethyl-13-aza-15-hydroxy-16-(4-propylphenylthio)-17,18,19,20-tetranor-11a-carbathromb-5-enoic acid or its methyl ester.

26. A compound according to claim 13 which is (5Z,15ξ)-9,11-methano-10,10-dimethyl-13-aza-15-hydroxy-16-(4-chlorophenylthio)-17,18,19,20-tetranor-11a-carbathromb-5-enoic acid or its methyl ester.

27. A compound according to claim 13 which is (5Z,15ξ)-9,11-methano-10,10-dimethyl-13-aza-15- hydroxy-16-(3-chlorophenylthio)-17,18,19,20-tetranor-11a-carbathromb-5-enoic acid or its methyl ester.

28. A compound according to claim 13 which is (5Z,15ξ)-9,11-methano-10,10-dimethyl-13-aza-15-hydroxy-16-(3-trifluorophenylthio)-17,18,19,20-tetranor-11a-carbathromb-5-enoic acid or its methyl ester.

29. A compound according to claim 3 wherein A represents

—CH$_2$CH$_2$—(CH$_2$)$_m$—

(in which m is as defined in claim 1).

30. A compound according to claim 29 which is (15ξ)-9,11-methano-10,10-dimethyl-13-aza-15-hydroxy-16-phenylthio-17,18,19,20-tetranor-11a-carbathrombanoic acid or its methyl ester.

31. A compound according to claim 3 wherein A represents

—CH$_2$—O—(CH$_2$)$_m$—

(in which m is as defined in claim 1).

32. A compound according to claim 31 which is (15ξ)-5-oxa-9,11-methano-10,10-dimethyl-13-aza-15-hydroxy-16-(4-ethylphenylthio)-17,18,19,20-tetranor-11a-carbathrombanoic acid or its methyl ester.

33. A compound according to claim 3 wherein A represents

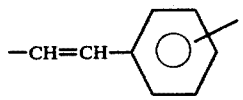

(in which the double bond and the phenylene group are as defined in claim 1).

34. A compound according to claim 33 which is (5EZ,15ξ)-1,5-inter-p-phenylene-9,11-methano-10,10-dimethyl-13-aza-15-hydroxy-16-(4-ethylphenylthio)-2,3,4,17,18,19,20-heptanor-11a-carbathromb-5-enoic acid or its methyl ester.

35. A compound according to claim 1 wherein R$^3$ represents a hydrogen atom.

36. A compound according to claim 35 wherein two R$^2$ both represent methyl groups.

37. A compound according to claim 36 wherein A represents

—CH$\overset{cis}{=\!=\!=}$CH—(CH$_2$)$_m$—

(in which m is as defined in claim 1).

38. A compound according to claim 37 which is (5Z)-9,11-methano-10,10-dimethyl-13-aza-11a-carbathromb-5-enoic acid or its methyl ester.

39. A compound according to claim 37 which is (5Z)-9,11-methano-10,10-dimethyl-13-aza-16-phenylthio-17,18,19,20-tetranor-11a-carbathromb-5-enoic acid or its methyl ester.

40. A compound according to claim 35 wherein two R$^2$ both represent hydrogen atoms.

41. A compound according to claim 40 which is (5Z)-9,11-methano-13-aza-11a-carbathromb-5-enoic acid or its methyl ester.

42. A pharmaceutical composition for the prevention and treatment of inflammation, hypertension thrombus, cerebral apoplexy, asthma, cardiac infarction, angina pectoris, and cerebral infarction, which comprises, as active agredient, an effective amount of at least one compound of the general formula V depicted in claim 1, wherein various symbols are as defined in claim 1, or a cyclodextrin clathrate thereof, or, when R$^1$ represents a hydrogen atom, a non-toxic salt thereof, together with a pharamceutical carrier or coating.

43. A method for the prevention and treatment of inflammation, hypertension thrombus, cerebral apoplexy, asthma, cardiac infarction, angina pectoris, and cerebral infarction, which comprises the oral, rectal, or parenteral administration of an effective amount of a compound as claimed in claim 1, a cyclodextrin clathrate thereof, or, when R$^1$ in formula V depicted in claim 1 represents a hydrogen atom, a non-toxic salt thereof.

* * * * *